US012767632B2

(12) United States Patent
Shen et al.

(10) Patent No.: US 12,767,632 B2
(45) Date of Patent: Oct. 20, 2026

(54) SELECTIVE HISTONE DEACETYLASE 6 INHIBITORS

(71) Applicants: The Board of Trustees of the University of Illinois, Urbana, IL (US); The George Washington University, A Congressionally Chartered Not-for-Profit Corporation, Washington, DC (US)

(72) Inventors: Sida Shen, Chicago, IL (US); Alejandro Villagra, Falls Church, VA (US); Alan Kozikowski, Chicago, IL (US)

(73) Assignees: The Board of Trustees of the University of Illinois, Urbana, IL (US); The George Washington University, A Congressionally Chartered Not-for-Profit Corporation, Washington, DC (US)

( * ) Notice: Subject to any disclaimer, the term of this patent is extended or adjusted under 35 U.S.C. 154(b) by 754 days.

(21) Appl. No.: 18/002,952

(22) PCT Filed: Jun. 25, 2021

(86) PCT No.: PCT/US2021/039195
§ 371 (c)(1),
(2) Date: Dec. 22, 2022

(87) PCT Pub. No.: WO2021/263171
PCT Pub. Date: Dec. 30, 2021

(65) Prior Publication Data

US 2023/0250054 A1 Aug. 10, 2023

Related U.S. Application Data

(60) Provisional application No. 63/044,407, filed on Jun. 26, 2020.

(51) Int. Cl.

| | |
|---|---|
| ***C07C 275/40*** | (2006.01) |
| ***A61K 31/17*** | (2006.01) |
| ***A61K 31/69*** | (2006.01) |
| ***A61K 39/395*** | (2006.01) |
| ***A61P 35/00*** | (2006.01) |
| ***C07F 5/02*** | (2006.01) |

(52) U.S. Cl.
CPC ............ *C07C 275/40* (2013.01); *A61K 31/17* (2013.01); *A61K 31/69* (2013.01); *A61K 39/3955* (2013.01); *A61P 35/00* (2018.01); *C07F 5/025* (2013.01)

(58) Field of Classification Search
CPC ....... C07C 275/40; A61P 35/00; A61K 31/17; A61K 31/69; C07F 5/025
See application file for complete search history.

(56) References Cited

U.S. PATENT DOCUMENTS

| | | | | |
|---|---|---|---|---|
| 9,382,197 | B2 | 7/2016 | Blackburn et al. | |
| 9,751,832 | B2 * | 9/2017 | Sotomayor | A61K 31/185 |
| 11,472,780 | B2 | 10/2022 | Villagra et al. | |
| 2015/0344466 | A1 | 12/2015 | Mitsudera et al. | |
| 2016/0185716 | A1 | 6/2016 | Sotomayor et al. | |
| 2020/0022966 | A1 | 1/2020 | Tang et al. | |

FOREIGN PATENT DOCUMENTS

| | | | | |
|---|---|---|---|---|
| JP | 2015510886 | A | 4/2015 | |
| WO | WO-2003050261 | A2 | 6/2003 | |
| WO | WO-03060523 | A1 | 7/2003 | |
| WO | WO-2003060523 | A1 | 7/2003 | |
| WO | WO-2006013209 | A2 * | 2/2006 | A61P 3/04 |
| WO | WO-2008055068 | A2 | 5/2008 | |
| WO | WO-2011106632 | A1 * | 9/2011 | C07D 491/048 |
| WO | WO-2015017546 | A1 | 2/2015 | |

(Continued)

OTHER PUBLICATIONS

Awad, Journal of Clinical Oncology, vol. 37, No. 15 Supplement, May 26, 2019 (Year: 2019).*

Tavares, ACS Med Chem, 2017, Supporting Information (Year: 2017).*

Porter, N.J., et al., "Unusual Zinc-binding Mode of HDAC6-selective Hydroxamate Inhibitors," Proceedings of the National Academy of Sciences of the United States of America 114(51):13459-13464, National Academy of Sciences, United States (Dec. 2017).

Abel, T. and Zukin, R. S., "Epigenetic targets of HDAC inhibition in neurodegenerative and psychiatric disorders," *Curr Opin Pharmacol.* 8(1):57-64, National Institute of Health, United States (2008).

Andrews, K.T., et al., "Anti-malarial effect of histone deacetylation inhibitors and mammalian tumour cytodifferentiating agents," Int. J. Parasitol. 30(6):761-768, Elsevier, Netherlands (2000).

(Continued)

*Primary Examiner* — Andrew D Kosar
*Assistant Examiner* — Phillip Matthew Rzeczycki
(74) *Attorney, Agent, or Firm* — Kory D. Christensen

(57) ABSTRACT

The present disclosure provides methods, pharmaceutical compositions, and kits comprising histone deacetylase (HD AC) inhibitors of formula I, or a pharmaceutically acceptable salt thereof, wherein $R^1$, $R^2$, $L^1$, $L^2$, m, n, p, X, Y, and Z are as defined in the specification, including methods of increasing the sensitivity of cancer cells to the cytotoxic effects of radiotherapy and/or chemotherapy in a subject.

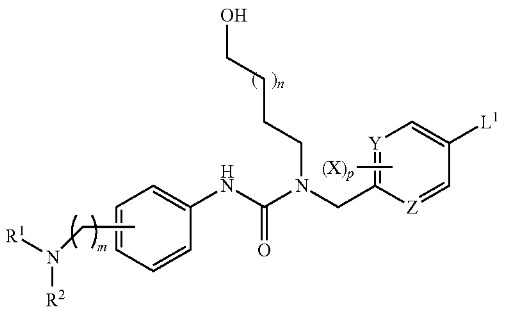

20 Claims, 9 Drawing Sheets

(56) References Cited

FOREIGN PATENT DOCUMENTS

| | | | |
|---|---|---|---|
| WO | WO-2017040564 | A1 | 3/2017 |
| WO | WO-2018183701 | A1 | 10/2018 |
| WO | WO-2020194272 | A1 | 10/2020 |
| WO | WO-2021263171 | A1 | 12/2021 |

OTHER PUBLICATIONS

Baltan, et al., "Novel Protective effects of Histone Deacetylase Inhibition on Stroke and White Matter Ischemic Injury," *Neurotherapeutics* 10:798-807, The American Society for Experimental Neuro Therapeutics, Inc., United States (2013).

Barlev, N.A., et al., "Acetylation of p53 Activates Transcription Through Recruitment of coactivators/histone Acetyltransferases," Mol. Cell 8(6):1243-1254, , American Society for Microbiology, United States (Dec. 2001).

Bergman, J.A., et al., "Selective Histone Deacetylase 6 Inhibitors Bearing Substituted Urea Linkers Inhibit Melanoma Cell Growth," J. Med. Chem. 55:9891-9899, American Chemical Society, United States (2012).

Bhatia, S., et al., "Discovery of the First-in-Class Dual Histone Deacetylase-Proteasome Inhibitor," J. Med. Chem. 61:10299-10309, American Chemical Society, United States (2018).

Bingham, A.L., et al., "Over one hundred solvates of sulfathiazole," Chem Commun (7): 603-604, Royal Society of Chemistry, England (Mar. 2001).

Bradley, M.O., et al., "Tumor targeting by covalent conjugation of a natural fatty acid to paclitaxel," Clin. Cancer Res. 7(10):3229-3238, American Association for Cancer Research, United States (2001).

Butler, K.V., et al., "Rational design and simple chemistry yield a superior, neuroprotective HDAC6 inhibitor, tubastatin A," J. Am. Chem. Soc. 132:10842-10846, American Chemical Society, United States (2010).

Caira, M,R., et al., "Preparation and Crystal Characterization of a Polymorph, a Monohydrate, and an Ethyl Acetate Solvate of the Antifungal Fluconazole," Journal of Pharmaceutical Sciences 93(3):601-611, American Pharmaceutical Assn, United States (Mar. 2004).

Cheng, F., et al., "A novel role for histone deacetylase 6 in the regulation of the tolerogenic STAT3/IL-10 pathway in APCs," J. Immunol. 193:2850-2862, American Association of Immunologists, United States (2014).

Choudhary, C., et al., "The growing landscape of lysine acetylation links metabolism and cell signaling," Nat. Rev. Mol. Cell Biol. 15:536-550, Nature Publishing Group, United Kingdom (2014).

Conti, P., et al., "Design and synthesis of novel isoxazole-based HDAC inhibitors," *European Journal of Medicinal Chemistry* 45:4331-4338, Elsevier Masson SAS, France (2010).

Daina, A., et al., "SwissADME: a free web tool to evaluate pharmacokinetics, drug-likeness and medicinal chemistry friendliness of small molecules," Sci. Rep. 7:42717, Nature Publishing Group, United Kingdom (2017).

Dal Maso, L., et al., "Epidemiology of non-Hodgkin lymphomas and other haemolymphopoietic neoplasms in people with AIDS," Lancet Oncol. 4(2):110-119, Elsevier, Netherlands (2003).

De Vreese, R., and D'Hooghe, M., "Synthesis and applications of benzohydroxamic acid-based histone deacetylase inhibitors," Eur. J. Med. Chem. 135:174-195, Elsevier, Netherlands (2017).

Didonna, A. and Opal, P., "The promise and perils of HDAC inhibitors in neurodegeneration," *Annals of Clinical and Translational Neurology* 2(1):79-101, John Wiley & Sons, Inc., United States (2015).

Dow, G.S., et al., "Antimalarial activity of phenylthiazolyl-bearing hydroxamate-based histone deacetylase inhibitors," *Antimicrobial Agents and Chemotherapy* 52(10):3467-3477, American Society for Microbiology, United States (2008).

Eckschlager, T., et al., "Histone Deacetylase Inhibitors as Anticancer Drugs," Int. J. Mol. Sci. 18:E1414, MDPI, Switzerland (2017).

El-Serag, H.B., "Hepatocellular carcinoma: an epidemiologic view," J. Clin. Gastroenterol 35(5 Suppl 2):S72-78, Wolters Kluwer, Switzerland (2002).

Extended European Search Report for EP Application No. EP 18776871, Munich, Germany, mailed on Mar. 5, 2021, 11 pages.

Falkenberg, K.J., et al., "Histone deacetylases and their inhibitors in cancer, neurological diseases and immune disorders," Nat. Rev. Drug Discov. 13(9):673-691, Nature Publishing Group, United States (2014).

Faria Freitas, M., et al., "HDAC inhibitors: a 2013-2017 patent survey," Expert Opin. Ther. Pat. 28:365-381, Taylor & Francis, United Kingdom (2018).

Gaisina, I.N., et al., "Identification of HDAC6-Selective Inhibitors of Low Cancer Cell Cytotoxicity," *ChemMedChem* 11:81-92, John Wiley and Sons Ltd, United Kingdom (2016).

Gu, W., et al., "Activation of p53 Sequence-Specific DNA Binding by Acetylation of the p53 C-terminal Domain," Cell 90(4):595-606, Cell Press, United States (Aug. 1997).

Hai, Y., et al., "Histone deacetylase 6 structure and molecular basis of catalysis and inhibition," Nat. Chem. Biol. 12(9):741-747, Nature Publishing Group, United Kingdom (2016).

Hernandez-Avila, M., et al., "Human papilloma virus 16-18 infection and cervical cancer in Mexico: a case-control study," Archives of Medical Research 28:265-271, Elsevier, Netherlands (1997).

Hermann, K., et al., "Epstein-Barr virus-associated carcinomas: facts and fiction," J. Pathol. 199(2):140-145, Wiley, United States (2003).

Hillgren, K.M., et al., "In vitro systems for studying intestinal drug absorption," Med. Res. Rev. 15(2):83-109, Wiley, United States (1995).

Hopkins, A.L., et al., "Ligand efficiency: a useful metric for lead selection," Drug Discov. Today 9(10):430-431, Elsevier, Netherlands (2004).

Huang, P., et al., "Selective HDAC inhibition by ACY-241 enhances the activity of paclitaxel in solid tumor models," *Oncotarget* 8(2):2694-2707, Impact Journals LLC, United States (2017).

Imai, Y., et al., "Action mechanisms of histone deacetylase inhibitors in the treatment of hematological malignancies," Cancer Sci. 107(11):1543-1549, Wiley, United States (2016).

International Search Report and Written Opinion in International Application No. PCT/US21/39195, mailed on Oct. 4, 2021, International Searching Authority, United States, 7 pages.

International Search Report and Written Opinion for Application No. PCT/US2018/025177, mailed on Aug. 1, 2018, 10 pages.

Ito, A., et al., "p300/CBP-mediated p53 acetylation is commonly induced by p53-activating agents and inhibited by MDM2," EMBO Journal 20(6):1331-1340, EMBO Press, Germany (Mar. 2001).

Ito, A., et al., "MDM2-HDAC1-mediated Deacetylation of p53 Is Required for Its Degradation," EMBO 21(22):6236-6245, EMBO Press, Germany (Nov. 2002).

Jochems, J., et al., "Antidepressant-like properties of novel HDAC6-selective inhibitors with improved brain bioavailability," *Neuropsychopharmacology* 39(2):389-400, Nature Publishing Group, United Kingdom (2014).

Johnson, T.W., et al., "Lipophilic Efficiency as an Important Metric in Drug Design," J. Med. Chem. 61(15):6401-6420, American Chemical Society, United States (2018).

Kadow, J.F., et al., "The role of viruses in human cancer development and antiviral approaches for intervention," Curr. Opin. Investig. Drugs 3(11):1574-1579, Current Drugs Ltd., United Kingdom (2002).

Kalin, J.H., et al., "Development and therapeutic implications of selective histone deacetylase 6 inhibitors," J. Med. Chem. 56(16):6297-6313, American Chemical Society, United States (2013).

Knox, T., et al., "Selective HDAC6 inhibitors improve anti-PD-1 immune checkpoint blockade therapy by decreasing the anti-inflammatory phenotype of macrophages and down-regulation of immunosuppressive proteins in tumor cells," Sci. Rep. 9:6136, Nature Publishing Group, United Kingdom (2019).

Koya, R.C., et al., "BRAF inhibitor vemurafenib improves the antitumor activity of adoptive cell immunotherapy," Cancer Res. 72:3928-3937, American Association for Cancer Research, United States (2012).

(56) References Cited

OTHER PUBLICATIONS

Li, Y., et al., "HDACs and HDAC Inhibitors in Cancer Development and Therapy," Cold Spring Harbor Perspect. Med. 6(10):a026831, Cold Spring Harbor Laboratory Press, United States (2016).
Liu, L., et al., "p53 Sites Acetylated in Vitro by PCAF and p300 Are Acetylated in Vivo in Response to DNA Damage," Mol Cell Biol 19(2):1202-1209, American Society for Microbiology, United States (Feb. 1999).
Lienlaf, M., et al., "Essential role of HDAC6 in the regulation of PD-L1 in melanoma," Mol. Oncol. 10(5):735-750, Wiley, United States (2016).
Lu, J., et al., "Histone deacetylase inhibitors ae neuroprotective and preserve NGF-mediated cell survival following traumatic brain injury," *PNAS* 110(26): 10747-10752, United States National Academy of Sciences, United States (2013).
Ma, Z., et al., "Asymmetric dipolar cycloaddition reactions: a practical, convergent synthesis of chiral pyrrolidines," Tetrahedron: Asymmetry 8(6):883-888, Elsevier, Netherlands (1997).
Machado-Vieira, R., et al., "Histone Deacetylases and Mood Disorders: Epigenetic Programming in Gene-environment Interactions," *CNS Neuroscience & Therapeutics* 17:699-704, Blackwell Publishing Ltd., United States (2011).
Matthias, P., et al., "HDAC6 a new cellular stress surveillance factor," Cell Cycle 7:7-10, Taylor & Francis, United Kingdom (2008).
Mithraprabhu, S., et al., "Histone deacetylase (HDAC) inhibitors as single agents induce multiple myeloma cell death principally through the inhibition of class I HDAC," *British Journal of Haematology* 162(4):559-62, John Wiley & Son Ltd., United Kingdom (2013).
Miyake, Y., et al., "Structural insights into HDAC6 tubulin deacetylation and its selective inhibition," Nat. Chem. Biol. 12:748-754, Nature Publishing Group, United Kingdom (2016).
Mortreux, F., et al., "Molecular and cellular aspects of HTLV-1 associated leukemogenesis in vivo," Leukemia 17(1):26-38, Nature Publishing Group, United Kingdom (2003).
Noonepalle, S., et al., "Rational Design of Suprastat: A Novel Selective Histone Deacetylase 6 Inhibitor with the Ability to Potentiate Immunotherapy in Melanoma Models," J. Med. Chem. 63:10246-10262, American Chemical Society, United States (2020).
O'Donnell, J.S., et al., "Resistance to PD1/PDL1 checkpoint inhibition," Cancer Treat. Rev. 52:71-81, Elsevier, Netherlands (2017).
Osko, J.D., et al., "Exploring Structural Determinants of Inhibitor Affinity and Selectivity in Complexes with Histone Deacetylase 6," J. Med. Chem. 63:295-308, American Chemical Society, United States (2020).
Osko, J.D., et al., "Structural determinants of affinity and selectivity in the binding of inhibitors to histone deacetylase 6," Bioorg. Med. Chem. Lett. 30:127023, Elsevier, Netherlands (2020).
Porter, N.J., et al., "Histone Deacetylase 6-Selective Inhibitors and the Influence of Capping Groups on Hydroxamate-Zinc Denticity," J. Med. Chem. 61:8054-8060, American Chemical Society, United States (2018).
Rebe, C., et al., "STAT3, a Master Regulator of Anti-Tumor Immune Response," Cancers (Basel) 11:1280, MDPI, Switzerland (2019).
Ren, J., et al., "Selective HDAC6 inhibition decreases early stage of lupus nephritis by down-regulating both innate and adaptive immune responses," *Clinical and Experimental Immunology* 191(1):19-31, Wiley-Blackwell Publishing Ltd, United Kingdom (2018).
Robbins, and Angell, Basic Pathology, $2^{nd}$ Edition, pp. 112-113, W.B. Saunders Co., United States (1976).
Saito, S., et al., "Tubastatin ameliorates pulmonary fibrosis by targeting the TGFβ-PI3K-Akt pathway," *PLoS One* 12(10):e0186615, Public Library of Science, United States (2017).
Sakaguchi, K., et al., "DNA Damage Activates p53 Through a Phosphorylation-Acetylation Cascade," Genes Dev. 12(18):2831-2841, Cold Spring Harbor Press, United States (Sep. 1998).
Santo, L., et al., "Preclinical activity, pharmacodynamic, and pharmacokinetic properties of a selective HDAC6 inhibitor, ACY-1215, in combination with bortezomib in multiple myeloma," *Blood* 119(11):2579-89, American Society of Hematology, United States (2012).
Shen, S., et al., "A patent review of histone deacetylase 6 inhibitors in neurodegenerative diseases (2014-2019)," Expert Opin. Ther. Pat. 30:121-136, Taylor & Francis, United Kingdom (2020).
Shen, S., et al., "Discovery of a New Isoxazole-3-hydroxamate-Based Histone Deacetylase 6 Inhibitor SS-208 with Antitumor Activity in Syngeneic Melanoma Mouse Models," J. Med. Chem. 62:8557-8577, American Chemical Society, United States (2019).
Shen, S., et al., "Structural and in Vivo Characterization of Tubastatin A, a Widely Used Histone Deacetylase 6 Inhibitor," ACS Med. Chem. Lett. 11(5):706-712, American Chemical Society, United States (2020).
Silverman, Chapter 8 in *The Organic Chemistry of Drug Design and Drug Action,* Academic Press, United States (1992).
Sixto-Lopez, Y., et al., "Structural and energetic basis for the inhibitory selectivity of both catalytic domains of dimeric HDAC6," J. Biomol. Struct. Dyn. 37:4701-4720, Taylor & Francis, United Kingdom (2019).
Supplementary European Search Report for EP Application No. EP 18 77 6871, Munich, Germany, mailed on Dec. 2, 2020, 15 pages.
Tang, J., et al., "Histone deacetylases as targets for treatment of multiple diseases," *Clin Sci* (*Lond*) 124(11):651-662, National Institute of Health, United States (2013).
Tapadar, et al., "Isoxazole moiety in the linker region of HDAC inhibitors adjacent to the Zn-chelating group: Effects on HDAC biology and antiproliferative activity," Bioorganic & Medicinal Chemistry Letters 19 (11):3023-3026, Elsevier, Netherlands (Jun. 2009).
Tao, R., et al., "Deacetylase inhibition promotes the generation and function of regulatory T cells," Nat. Med. 13:1299-1307, Nature Publishing Group, United Kingdom (2007).
Tavares, M.T., et al., "Synthesis and Pharmacological Evaluation of Selective Histone Deacetylase 6 Inhibitors in Melanoma Models," ACS Med. Chem. Lett. 8:1031-1036, American Chemical Society, United States (2017).
Van Tonder, E.C., et al., "Preparation and Physicochemical Characterization of 5 Niclosamide Solvates and 1 Hemisolvate," AAPS PharmSciTech 5(1):E12, American Association of Pharmaceutical Scientists, United States (Feb. 2004).
Vogerl, K., et al., "Synthesis and Biological Investigation of Phenothiazine-Based Benzhydroxamic Acids as Selective Histone Deacetylase 6 Inhibitors," J. Med. Chem. 62(3):1138-1166, American Chemical Society, United States (2019).
Volmar, C-H. and Wahlestedt, C., "Histone deacetylases (HDACs) and brain function," *Neuroepigenetics* 1:20-27, Elsevier, Netherlands (2015).
Wang, Q., et al., "Acetylation of metabolic enzymes coordinates carbon source utilization and metabolic flux," Science 327(5968):1004-1007, American Association for the Advancement of Science, United States (2010).
Wang, X.X., et al., "Recent advances in the discovery of potent and selective HDAC6 inhibitors," Eur. J. Med. Chem. 143:1406-1418, Elsevier, Netherlands (2018).
Woan, K.V., et al., "Targeting histone deacetylase 6 mediates a dual anti-melanoma effect: Enhanced antitumor immunity and impaired cell proliferation," Mol. Oncol. 9:1447-1457, Wiley, United States (2015).
Yang, F., et al., "Next-generation of selective histone deacetylase inhibitors," *RSC Advances* 9:19571-19583, Royal Society of Chemistry, United Kingdom (2019).
Zhao, S., et al., "Regulation of cellular metabolism by protein lysine acetylation," Science 327:1000-1004, American Association for the Advancement of Science, United States (2010).

* cited by examiner

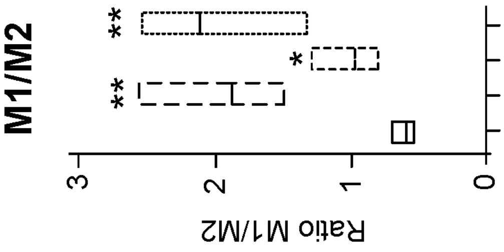
FIG. 6C
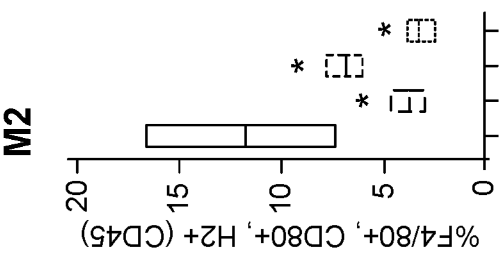
FIG. 6B
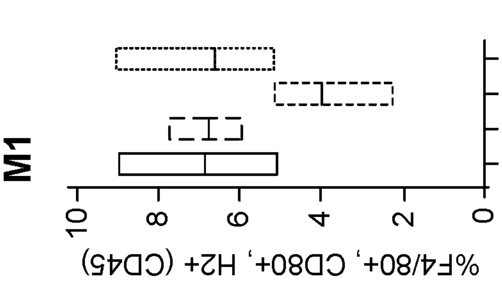
FIG. 6A

SELECTIVE HISTONE DEACETYLASE 6 INHIBITORS

STATEMENT OF GOVERNMENTAL INTEREST

This invention was made with government support under grant no. 5R01 NS079183 awarded by the National Institutes of Health. The U.S. government has certain rights in the invention.

TECHNICAL FIELD

This disclosure relates to histone deacetylase (HDAC) inhibitors, for example, to selective HDAC6 inhibitors, to pharmaceutical compositions comprising one or more of the HDAC inhibitors, to methods of increasing the sensitivity of cancer cells to the cytotoxic effects of radiotherapy and/or chemotherapy comprising contacting the cell with one or more of the HDAC inhibitors, and to therapeutic methods of treating conditions and diseases wherein inhibition of HDAC provides a benefit, for example, a cancer, an inflammation, a neurological disease, a neurodegenerative disorder, stroke, traumatic brain injury, allograft rejection, autoimmune diseases, and malaria, comprising administering a therapeutically effective amount of a present HDAC inhibitor to an individual in need thereof.

BACKGROUND OF THE INVENTION

Reversible acetylation of lysine side chains on the surfaces of enzymes and other proteins is regulated by histone acetyltransferases (HATs) and histone deacetylases (HDACs). Protein lysine acetylation or deacetylation serves as a critical regulatory pathway for diverse cellular processes such as transcription, cell cycle, and cellular metabolism (see, e.g., Zhao et al., *Science* 327: 1000-1004 (2010); Wang et al., *Science* 327: 1004-1007 (2010); or Choudhary et al., *Nat. Rev. Mol. Cell Biol.* 15: 536-550, (2014)). HDACs are considered as effective targets for therapeutic intervention in cancer treatment, neurological diseases, and immune disorders (see, e.g., Li et al., *Cold Spring Harb. Perspect. Med.* 6 (2016); Eckschlager et al., *Int. J. Mol. Sci.* 18: E1414 (2017); or Falkenberg et al., *Nat. Rev. Drug Discov.* 13: 673-691 (2014)). Up to date, 11 zinc ion ($Zn^{2+}$)-dependent HDACs (Class I, II, and IV) and seven nicotinamide adenine dinucleotide ($NAD^+$)-dependent sirtuins (SIRTs) (Class III) have been identified. Unlike other members, HDAC6 in Class IIb subgroup is unique due to its ability to deacetylate a variety of non-histone proteins as its preferred substrates, such as α-tubulin, cortactin, HSP-90, and HSF-1 (see, e.g., Matthias et al., *Cell Cycle* 7: 7-10 (2008); or Imai et al., *Cancer Sci.* 107: 1543-1549 (2016)). As three HDAC6 inhibitors (HDAC6is), Ricolinostat (ACY-1215), Citarinostat (ACY-241), and KA2507 are being investigated in clinical trials for various types of cancers through either monotherapy or a combination approach (see, e.g., Shen et al., *Expert Opin. Ther. Pat.* 30: 121-136 (2020)), HDAC6is have been developed and emerged as a promising approach for cancer therapy.

Immunomodulatory properties of HDAC6s have deemed them as novel therapeutic agents for cancer immunotherapy. It has been reported that HDAC6 interacts with transcription factor STAT3, a master regulator of immune responses in the tumor microenvironment (see, e.g., Rebe et al., *Cancers (Basel)* 11: 1280 (2019)), and regulates STAT3-mediated gene expression (see, e.g., Cheng et al., *J. Immunol.* 193: 2850-2862 (2014)). In antigen-presenting cells (APCs) such as macrophages and dendritic cells, selective inhibition of HDAC6 leads to a decreased production of immunosuppressive cytokine IL-10, thereby retaining the proinflammatory state of APCs (see, e.g., Cheng et al., *J. Immunol.* 193: 2850-2862 (2014)). In melanoma tumor cells, HDAC6 inhibition results in a decreased expression of immunosuppressive molecule PD-L1 by affecting the recruitment and activation of STAT3 (see, e.g., Lienlaf et al., *Mol. Oncol.* 10: 735-750 (2016)). Furthermore, using a syngeneic murine melanoma mouse model, it has been demonstrated that combination therapy of selective HDAC6i and PD-1 antibody led to significantly improved effects on tumor growth compared to single therapy (see, e.g., Knox et al., *Sci. Rep.* 9: 6136 (2019)), thereby underscoring the immunomodulatory capability of selective HDAC6 inhibitors.

SUMMARY OF THE INVENTION

The present disclosure relates to histone deacetylase inhibitors (HDACIs), pharmaceutical compositions comprising the HDACI, and methods of treating diseases and conditions wherein inhibition of HDAC provides a benefit, such as a cancer, a neurological disease, a psychiatric illness, a neurodegenerative disorder, a peripheral neuropathy, stroke, hypertension, an inflammation, traumatic brain injury, rheumatoid arthritis, allograft rejection, sepsis, and autoimmune diseases, comprising administering a therapeutically effective amount of an HDACI to an individual in need thereof. The present disclosure also relates to a method of increasing the sensitivity of a cancer cell to radiotherapy and/or chemotherapy. The present disclosure also allows for the use of these HDAC inhibitors in combination with other drugs and/or therapeutic approaches. In some embodiments, the present HDACIs exhibit selectivity for HDAC isozymes, such as HDAC6, over other HDAC isozymes. In certain embodiments, this disclosure relates to phenylhydroxamic acids that selectively inhibit HDAC6. In other embodiments, this disclosure relates to use of the inhibitors in combination with anti-PD1 immunotherapy for treatment of cancer.

In some embodiments, the present disclosure relates to histone deacetylase inhibitors (HDACIs) having a structural formula I.

I

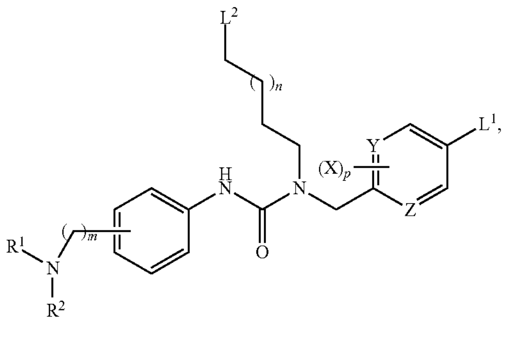

wherein $R^1$ and $R^2$ are independently selected from the group consisting of hydrogen and $C_1$-$C_6$ alkyl, or $R^1$ and $R^2$ are joined to form a 3-7 membered heterocyclyl; $L^1$ is $CO_2H$, $C(O)NH_2$, $C(O)NHOH$, or $B(OH)_2$; $L^2$ is H or $OR^3$; $R^3$ is selected from the group consisting of hydrogen, acetyl, $C_1$-$C_6$ alkyl, $C_1$-$C_6$ haloalkyl, $C_3$-$C_6$ cycloalkyl, aryl, heteroaryl, and $C_5$-$C_6$ heterocyclyl; each X is independently hydrogen or halogen; p is 0, 1, 2, or 3; Y and Z are independently selected from the group consisting of carbon and nitrogen; m is 1, 2, 3 or 4; and n is 0, 1 or 2. In another embodiment, $R^1$, $R^2$ and $R^3$ are independently $C_1$-$C_6$ branched alkyl.

BRIEF DESCRIPTION OF THE DRAWINGS

FIG. 6A is a boxplot graph showing macrophage 1 cells stained with cell surface markers and analyzed by multi-color flow cytometry after treatment with Suprastat or anti-PD1 therapy or a combination of both.

FIG. 6B is a boxplot graph showing macrophage 2 cells stained with cell surface markers and analyzed by multi-color flow cytometry after treatment with Suprastat or anti-PD1 therapy or a combination of both.

FIG. 6C is a boxplot graph showing macrophage 1/macrophage 2 cells stained with cell surface markers and analyzed by multi-color flow cytometry after treatment with Suprastat or anti-PD1 therapy or a combination of both.

DETAILED DESCRIPTION OF THE INVENTION

Figure 1A:
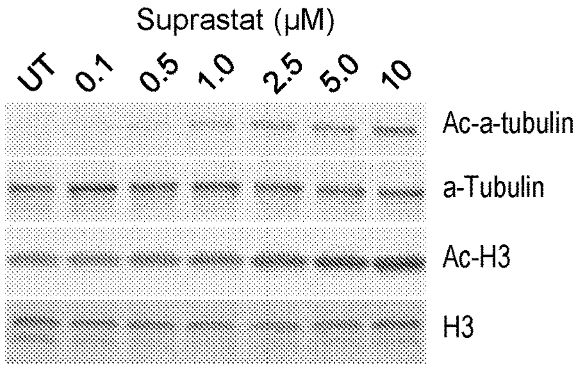
FIG. 1A is an illustration showing the immunoblot analysis in WM164 human melanoma cells treated overnight with increasing concentrations ranging from 0.1 μM to 10 μM of Suprastat (6a). The analysis was performed for Ac-α-tubulin and Ac—H3. Total α-tubulin and total H3 are loading controls. The immunoblots were repeated at least twice for the robustness of the data, and the best representation is shown.
Figure 1B:
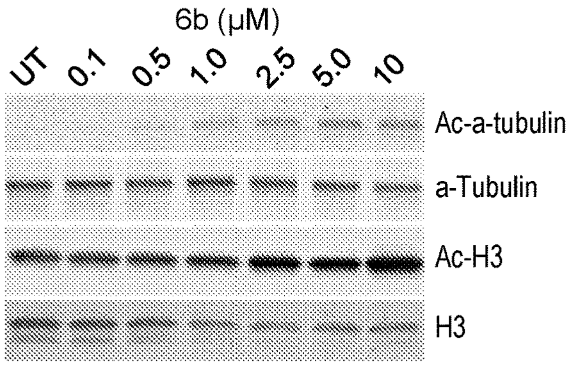
FIG. 1B is an illustration showing the immunoblot analysis in WM164 human melanoma cells treated overnight with increasing concentrations ranging from 0.1 μM to 10 μM of compound 6b. The analysis was performed for Ac-α-tubulin and Ac—H3. Total α-tubulin and total H3 are loading controls. The immunoblots were repeated at least twice for the robustness of the data, and the best representation is shown.
Figure 1C:
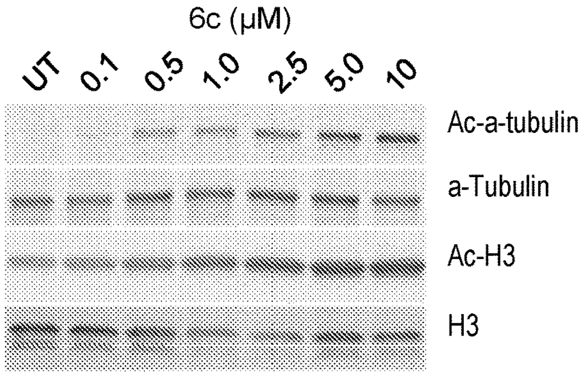
FIG. 1C is an illustration showing the immunoblot analysis in WM164 human melanoma cells treated overnight with increasing concentrations ranging from 0.1 μM to 10 μM of compound 6c. The analysis was performed for Ac-α-tubulin and Ac—H3. Total α-tubulin and total H3 are loading controls. The immunoblots were repeated at least twice for the robustness of the data, and the best representation is shown.
Figure 1D:
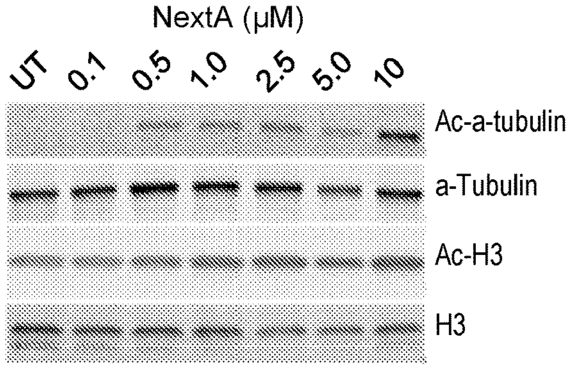
FIG. 1D is an illustration showing the immunoblot analysis in WM164 human melanoma cells treated overnight with increasing concentrations ranging from 0.1 μM to 10 μM of NextA. The analysis was performed for Ac-α-tubulin and Ac—H3. Total α-tubulin and total H3 are loading controls. The immunoblots were repeated at least twice for the robustness of the data, and the best representation is shown.

This disclosure is directed to novel HDAC inhibitors (HDACIs) and their use in therapeutic treatments of, for example, cancers, inflammations, traumatic brain injuries, neurodegenerative disorders, neurological diseases, peripheral neuropathies, strokes, hypertension, autoimmune diseases, inflammatory diseases, and malaria. The present HDACIs also increase the sensitivity of a cancer cell to the cytotoxic effects of radiotherapy and/or chemotherapy. In some embodiments, the present HDACIs selectively inhibit HDAC6 over other HDAC isozymes.

The disclosure is described in connection with preferred embodiments. However, it should be appreciated that the disclosure is not limited to the disclosed embodiments. It is understood that, given the description of the embodiments of the disclosure herein, various modifications can be made by a person skilled in the art. Such modifications are encompassed by the claims below.

Definitions

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$ alkyl indicate the same functionality; similarly arylalkyl and -alkylaryl indicate the same functionality.

"Acetyl" means a group of formula $CH_3C(O)$—.

"Alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

"Alkyl" means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

"Aryl," means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, and the like. The aryl is attached to the parent molecular moiety through any carbon atom contained within the aryl ring system. In certain embodiments, the aryl group is phenyl or naphthyl. In certain other embodiments, the aryl group is phenyl.

"Cycloalkyl" as used herein, means a monocyclic cycloalkyl ring system. Monocyclic ring systems are cyclic hydrocarbon groups containing from 3 to 6 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl and cyclohexenyl.

"Halo" or "halogen" means —Cl, —Br, —I or —F.

"Haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

"Heteroaryl" means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. In certain embodiments of the disclosure, the heteroaryl group is furyl, imidazolyl, pyridinyl, pyrimidinyl, pyrazinyl, pyrazolyl, pyrrolyl, thiazolyl, thienyl, triazolyl, benzimidazolyl, benzofuranyl, indazolyl, indolyl, quinolinyl, and the like.

"Heterocyclyl" means a monocyclic 5 or 6 membered heterocyclic ring containing at least one N atom and optionally one or more additional heteroatoms independently selected from the group consisting of O, N, and S where the ring is saturated or unsaturated, but not aromatic. Representative examples of monocyclic heterocycle include, but are not limited to, imidazolinyl, imidazolidinyl, isothiazolinyl, isothiazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, thiopyranyl. In certain embodiments, the heterocyclyl is imidazolinyl, pyrrolidinyl, piperidinyl, or piperazinyl.

This disclosure is directed to novel HDACIs of formula I, Ib, and Ic and their use in therapeutic treatments of, for example, cancers, inflammations, traumatic brain injuries, neurodegenerative disorders, neurological diseases, peripheral neuropathies, strokes, hypertension, autoimmune diseases, inflammatory diseases, and malaria. The present HDACIs also increase the sensitivity of a cancer cell to the cytotoxic effects of radiotherapy and/or chemotherapy. In some embodiments, the present HDACIs selectively inhibit HDAC6 over other HDAC isozymes.

The term "a disease or condition wherein inhibition of HDAC provides a benefit" pertains to a condition in which HDAC and/or the action of HDAC is important or necessary, e.g., for the onset, progress, expression of that disease or condition, or a disease or a condition which is known to be treated by an HDAC inhibitor (such as, e.g., TSA, pivaloyloxymethylbutane (AN-9; Pivanex), FK-228 (Depsipeptide), PXD-101, NVP-LAQ824, SAHA, MS-275, and or MGCD0103). Examples of such conditions include, but are not limited to, cancer, psoriasis, fibroproliferative disorders (e.g., liver fibrosis), smooth muscle proliferative disorders (e.g., atherosclerosis, restenosis), neurodegenerative diseases (e.g., Alzheimer's, Parkinson's, Huntington's chorea, amyotropic lateral sclerosis, spino-cerebellar degeneration, Rett syndrome), peripheral neuropathies (Charcot-Marie-Tooth disease, Giant Axonal Neuropathy (GAN)), inflammatory diseases (e.g., osteoarthritis, rheumatoid arthritis, colitis), diseases involving angiogenesis (e.g., cancer, rheumatoid arthritis, psoriasis, diabetic retinopathy), hematopoietic disorders (e.g., anemia, sickle cell anemia, thalasseimia), fungal infections, parasitic infections (e.g., malaria, trypanosomiasis, helminthiasis, protozoal infections), bacterial infections, viral infections, and conditions treatable by immune modulation (e.g., multiple sclerosis, autoimmune diabetes, lupus, atopic dermatitis, allergies, asthma, allergic rhinitis, inflammatory bowel disease; and for improving grafting of transplants). One of ordinary skill in the art is readily able to determine whether a compound treats a disease or condition mediated by HDAC for any cell type, for example, by assays which conveniently can be used to assess the activity of compounds.

"Second therapeutic agent" refers to a therapeutic agent different from a present HDACI and that is known to treat the disease or condition of interest. For example, when a cancer is the disease or condition of interest, the second therapeutic agent can be a known chemotherapeutic drug, like taxol, or radiation, for example.

"HDAC" refers to a family of enzymes that remove acetyl groups from a protein, for example, the ε-amino groups of lysine residues at the N-terminus of a histone. The HDAC can be a human HDAC, including, HDAC1, HDAC2, HDAC3, HDAC4, HDAC5, HDAC6, HDAC7, HDAC8, HDAC9, HDAC10, and HDAC11. The HDAC also can be derived from a protozoal or fungal source.

"Treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the disclosure to an individual in need of such treatment. A treatment can be orientated symptomatically, for example, to suppress symptoms. It can be effected over a short period, be oriented over a medium term, or can be a long-term treatment, for example within the context of a maintenance therapy.

The terms "therapeutically effective amount" or "effective dose" refer to an amount of the active ingredient(s) that, when administered, is (are) sufficient, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce HDAC signaling in the target cells; and/or relieve, to some extent, one or more of the symptoms associated with the cancer. To extent the administered compound or composition prevents growth and/or kills existing cancer cells, it may be cytostatic and/or cytotoxic.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a present HDACI can be administered at the same time or sequentially in any order at different points in time as a second therapeutic agent. A present HDACI and the second therapeutic agent can be administered separately, in any appropriate form and by any suitable route. When a present HDACI and the second therapeutic agent are not administered concurrently, it is understood that they can be administered in any order to a subject in need thereof. For example, a present HDACI can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a present HDACI and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely serve as a shorthand method of referring individually to each separate value falling within the range, unless otherwise indicated herein, and each separate value and subrange is incorporated into the specification as if it were individually recited herein. The use of any and all examples, or exemplary language (e.g., "such as" and "like") provided herein, is intended to better illustrate the disclosure and is not a limitation on the scope of the disclosure unless otherwise claimed. No language in the specification should be construed as indicating any non-claimed element as essential to the practice of the disclosure.

In some embodiments, the present disclosure is directed to HDACIs, compositions comprising the present HDACI, and therapeutic uses of the HDACIs of formula I.

I

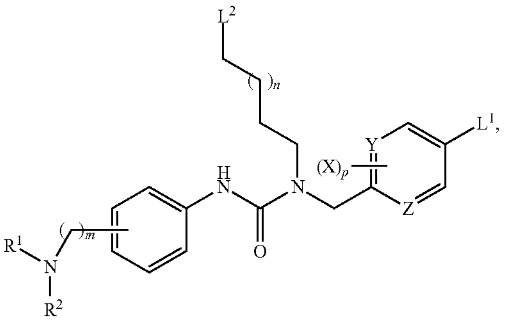

wherein $R^1$ and $R^2$ are independently selected from the group consisting of hydrogen and $C_1$-$C_6$ alkyl, or $R^1$ and $R^2$ are joined to form a 3-7 membered heterocyclyl; $L^1$ is $CO_2H$, $C(O)NH_2$, C(O)NHOH, or $B(OH)_2$; $L^2$ is H or $OR^3$; $R^3$ is selected from the group consisting of hydrogen, acetyl, $C_1$-$C_6$ alkyl, $C_1$-$C_6$ haloalkyl, $C_3$-$C_6$ cycloalkyl, aryl, heteroaryl, and $C_5$-$C_6$ heterocyclyl; each X is independently hydrogen or halogen; p is 0, 1, 2, or 3; Y and Z are independently selected from the group consisting of carbon and nitrogen; m is 1, 2, 3 or 4; and n is 0, 1 or 2. In another embodiment, $R^1$, $R^2$ and $R^3$ are independently $C_1$-$C_6$ branched alkyl.

In certain embodiments, $L^1$ is C(O)NHOH.

In other embodiments, the present disclosure is directed to HDACIs, compositions comprising the present HDACI, and therapeutic uses of the HDACIs of formula Ib:

Ib

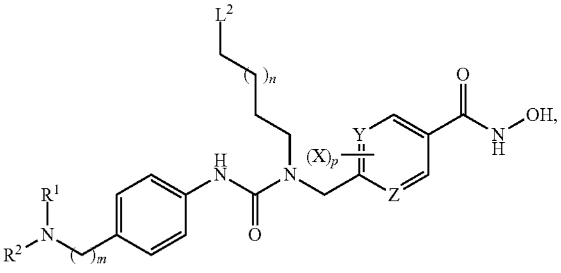

wherein $R^1$ and $R^2$ are independently selected from the group consisting of hydrogen and $C_1$-$C_6$ alkyl, or $R^1$ and $R^2$ are joined to form a 3-7 membered heterocyclyl; $L^2$ is H or $OR^3$; $R^3$ is selected from the group consisting of hydrogen, acetyl, $C_1$-$C_6$ alkyl, $C_1$-$C_6$ haloalkyl, $C_3$-$C_6$ cycloalkyl, aryl, heteroaryl, and $C_5$-$C_6$ heterocyclyl; each X is independently hydrogen or halogen; p is 0, 1, 2, or 3; Y and Z are selected from the group consisting of carbon and nitrogen; m is 1, 2, 3 or 4; and n is 0, 1 or 2. In another embodiment, $R^1$, $R^2$ and $R^3$ are independently $C_1$-$C_6$ branched alkyl.

In other embodiments, the present disclosure is directed to HDACIs, compositions comprising the present HDACI, and therapeutic uses of the HDACIs of formula Ic:

Ic

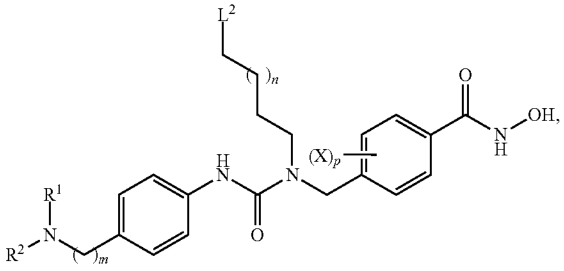

wherein $R^1$ and $R^2$ are independently selected from the group consisting of hydrogen and $C_1$-$C_6$ alkyl, or $R^1$ and $R^2$ are joined to form a 3-7 membered heterocyclyl; $L^2$ is H or $OR^3$; $R^3$ is selected from the group consisting of hydrogen, acetyl, $C_1$-$C_6$ alkyl, $C_1$-$C_6$ haloalkyl, $C_3$-$C_6$ cycloalkyl, aryl, heteroaryl, and $C_5$-$C_6$ heterocycloalkyl; each X is independently hydrogen or halogen; p is 0, 1, 2, or 3; m is 1, 2, 3 or 4; and n is 0, 1 or 2. In another embodiment, $R^1$, $R^2$ and $R^3$ are independently $C_1$-$C_6$ branched alkyl.

In other embodiments, the present disclosure is directed to HDACIs, compositions comprising the present HDACI, and therapeutic uses of the HDACIs of formula Id:

Id

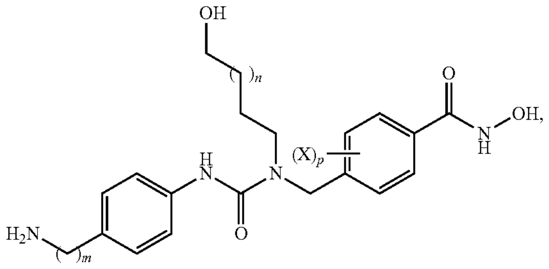

wherein each X is independently hydrogen or halogen; m is 1, 2, 3 or 4; p is 0, 1, 2, or 3; m is 1, 2, 3 or 4; and n is 0, 1 or 2.

In other embodiments, the present disclosure is directed to HDACIs, compositions comprising the present HDACI, and therapeutic uses of the HDACIs of formula Ie:

Ie

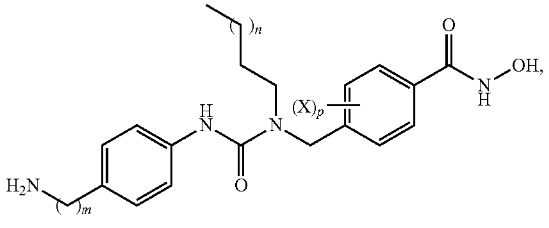

wherein each X is independently hydrogen or halogen; p is 0, 1, 2, or 3; m is 1, 2, 3 or 4; and n is 0, 1 or 2.

In other embodiments, the present disclosure is directed to the following HDACIs

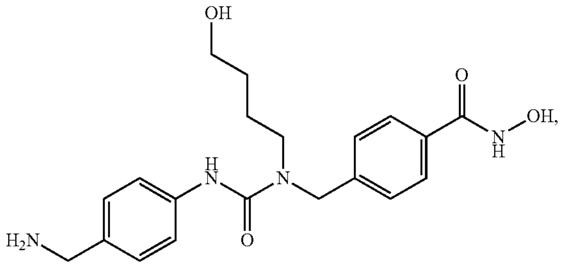

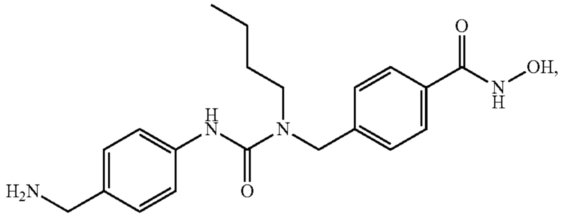

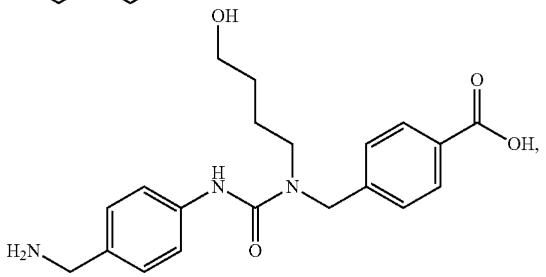

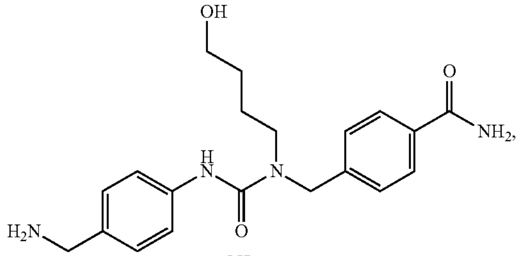

or

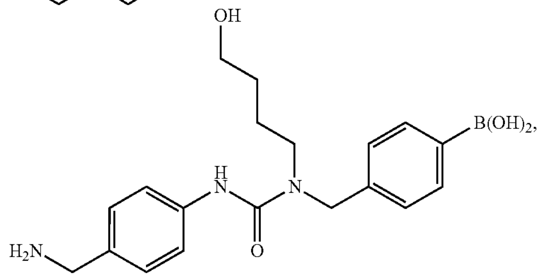

compositions comprising these HDACIs, and therapeutic uses of these HDACIs.

Additionally, salts, prodrugs, hydrates, isotopically labeled, fluorescently labeled and any other therapeutically or diagnostically relevant derivations of the present HDACIs also are included in the present disclosure and can be used in the methods disclosed herein. The present disclosure further includes all possible stereoisomers and geometric isomers of the present compounds. The present disclosure includes both racemic compounds and optically active isomers. When a present HDACI is desired as a single enantiomer, it can be obtained either by resolution of the final product or by stereospecific synthesis from either isomerically pure starting material or use of a chiral auxiliary reagent, for example, see Ma et al., *Tetrahedron: Asymmetry* 8: 883-888 (1997). Resolution of the final product, an intermediate, or a starting material can be achieved by any suitable method known in the art. Additionally, in situations where tautomers of a present compound is possible, the present disclosure is intended to include all tautomeric forms of the compounds.

Prodrugs of the present compounds also are included in the present disclosure. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, e.g., Bundgaard, Ed., "Design of Prodrugs," Elsevier, Amsterdam, (1985); Silverman, "The Organic Chemistry of Drug Design and Drug Action," Academic Press, San Diego, chapter 8, (1992); or Hillgren et al., *Med. Res. Rev.* 15: 83 (1995)). Specific prodrugs of HDACIs are discussed in WO 2008/055068, incorporated in its entirety herein by reference.

Compounds of the disclosure can exist as salts. Pharmaceutically acceptable salts of the present HDACIs often are preferred in the methods of the disclosure. As used herein, the term "pharmaceutically acceptable salts" refers to salts or zwitterionic forms of the present compounds. Salts of the present compounds can be prepared during the final isolation and purification of the compounds or separately by reacting the compound with an acid having a suitable cation. The pharmaceutically acceptable salts of the present compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of the present disclosure appearing herein is intended to include the present compounds as well as pharmaceutically acceptable salts, hydrates, or prodrugs thereof.

The present compounds also can be conjugated or linked to auxiliary moieties that promote a beneficial property of the compound in a method of therapeutic use. Such conjugates can enhance delivery of the compounds to an anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies, such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., *Clin. Cancer Res.* 7: 3229 (2001)).

Compounds of the present disclosure inhibit HDAC and are useful in the treatment of a variety of diseases and conditions. In some embodiments, the present HDACIs are used in methods of treating a disease or condition wherein inhibition of HDAC provides a benefit, for example, cancers, neurological diseases, neurodegenerative conditions, peripheral neuropathies, autoimmune diseases, inflammatory diseases and conditions, stroke, hypertension, traumatic brain injury, autism, and malaria. The methods comprise administering a therapeutically effective amount of a present HDACI to an individual in need thereof.

The present compounds have been evaluated for their activity at HDAC6 and their selectivity for HDAC6 compared to HDAC1. It previously was shown that selective HDAC6 inhibitors are implicated in a variety of disease states including, but not limited to, arthritis, autoimmune disorders, inflammatory disorders, cancer, neurological diseases such as Rett syndrome, peripheral neuropathies such as CMT, stroke, hypertension, and diseases in which oxidative stress is a causative factor or a result thereof. It also was shown that selective HDAC6 inhibitors, when administered in combination with rapamycin, prolonged the lifespan of mice with kidney xenografts. This model was used to evaluate the immunosuppressant properties of the present compounds and serve as a model of transplant rejection. Furthermore, it was previously shown that selective HDAC6 inhibitors confer neuroprotection in rat primary cortical neuron models of oxidative stress. These studies identified selective HDAC6 inhibitors as non-toxic neuroprotective agents. The present compounds behave in a similar manner because they also are selective HDAC6 agents. The present compounds demonstrate a ligand efficiency that renders them more drug-like in their physiochemical properties. In addition, the present compounds maintain the potency and selectivity observed in prior HDACIs. The present compounds therefore are pharmaceutical candidates and research tools to identify the specific functions of HDAC6.

Thus, in one embodiment, the present disclosure relates to a method of treating an individual suffering from a disease or condition wherein inhibition of HDAC provides a benefit comprising administering a therapeutically effective amount of a claimed HDACI compound to an individual in need thereof.

The methods of the present disclosure can be accomplished by administering one of the HDACI of the present disclosure as the neat compound or as a pharmaceutical composition. Administration of a pharmaceutical composition, or a neat HDACI of the present disclosure, can be performed during or after the onset of the disease or condition of interest. Typically, the pharmaceutical compositions are sterile, and contain no toxic, carcinogenic, or mutagenic compounds that would cause an adverse reaction when administered.

In some embodiments, a present HDACI may be administered in conjunction with a second therapeutic agent useful in the treatment of a disease or condition wherein inhibition of HDAC provides a benefit. The second therapeutic agent is different from the present HDACI. The second therapeutic agent is selected from agents, such as drugs and adjuvants, known as useful in treating the disease or condition afflicting the individual, e.g., a chemotherapeutic agent and/or radiation known as useful in treating a cancer. A present HDACI and the second therapeutic agent can be administered together as a single-unit dose or separately as multi-unit doses, wherein the present HDACI is administered simultaneously with, before the second therapeutic agent or vice versa. One or more doses of a present HDACI and/or one or more doses of the second therapeutic agent can be administered.

The second therapeutic agent is administered in an amount to provide its desired therapeutic effect. The effective dosage range for each second therapeutic agent is known in the art, and the second therapeutic agent is administered to an individual in need thereof within such established ranges.

The present disclosure therefore is directed to compositions and methods of using such compounds in treating diseases or conditions wherein inhibition of HDAC provides a benefit. The present disclosure also is directed to pharmaceutical compositions comprising a present HDACI and an optional second therapeutic agent useful in the treatment of diseases and conditions wherein inhibition of HDAC provides a benefit. Further provided are kits comprising a present HDACI and, optionally, a second therapeutic agent useful in the treatment of diseases and conditions wherein inhibition of HDAC provides a benefit, packaged separately or together, and an insert having instructions for using these active agents.

Within the meaning of the present disclosure, the term "disease" or "condition" denotes disturbances and/or anomalies that as a rule are regarded as being pathological conditions or functions, and that can manifest themselves in the form of signs, symptoms, and/or malfunctions. As demonstrated below, a present HDACI is a potent inhibitor of HDAC and can be used in treating diseases and conditions wherein inhibition of HDAC provides a benefit, for example, cancer, a neurological disease, a neurodegenerative condition, traumatic brain injury, stroke, an inflammation, an autoimmune disease, and autism.

In one embodiment, the present disclosure provides methods for treating cancer, including but not limited to killing a cancer cell or neoplastic cell; inhibiting the growth of a cancer cell or neoplastic cell; inhibiting the replication of a cancer cell or neoplastic cell; or ameliorating a symptom thereof, said methods comprising administering to a subject in need thereof an amount of a present HDACI or a pharmaceutically acceptable salt thereof sufficient to treat the cancer. Additionally, it is noted that the selective HDACI may be able to facilitate the killing of cancer cells through reactivation of the immune system by mechanisms relating to the PDI receptor. A present HDACI can be used as the sole anticancer agent, or in combination with another anticancer treatment, e.g., radiation, chemotherapy, and surgery.

In another embodiment, the disclosure provides a method for increasing the sensitivity of a cancer cell to the cytotoxic effects of radiotherapy and/or chemotherapy comprising contacting the cell with a present HDACI or a pharmaceutically acceptable salt thereof in an amount sufficient to increase the sensitivity of the cell to the cytotoxic effects of radiotherapy and/or chemotherapy.

In a further embodiment, the present disclosure provides a method for treating cancer comprising: (a) administering to an individual in need thereof an amount of a present HDACI compound; and (b) administering to the individual an amount of radiotherapy, chemotherapy, or both. The amounts administered are each effective to treat cancer. In another embodiment, the amounts are together effective to treat cancer.

This combination therapy of the disclosure can be used accordingly in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy and/or chemotherapy or is known to be responsive to radiotherapy and/or chemotherapy. Such cancers include, but are not limited to, non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, or other CNS neoplasms.

In still another embodiment, the cancer being treated has demonstrated resistance to radiotherapy and/or chemotherapy or is known to be refractory to radiotherapy and/or chemotherapy. A cancer is refractory to a therapy when at least some significant portion of the cancer cells are not killed or their cell division is not arrested in response to therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced or has increased.

Other cancers that can be treated with the compounds and methods of the disclosure include, but are not limited to, cancers and metastases, such as brain cancers (gioblastomas) and melanomas, as well as other common tumors.

In a specific embodiment, leukoplakia, a benign-appearing hyperplastic or dysplastic lesion of the epithelium, and Bowen's disease, a carcinoma in situ, are pre-neoplastic lesions indicative of the desirability of prophylactic intervention.

In another embodiment, fibrocystic disease (cystic hyperplasia, mammary dysplasia, and adenosis (benign epithelial hyperplasia)), is indicative of the desirability of prophylactic intervention.

The prophylactic use of the compounds and methods of the present disclosure are also indicated in some viral infections that may lead to cancer. For example, human papilloma virus can lead to cervical cancer (see, e.g., Hernandez-Avila et al., *Archives of Medical Research* 28: 265-271 (1997)), Epstein-Barr virus (EBV) can lead to lymphoma (see, e.g., Herrmann et al., *J Pathol* 199(2): 140-5 (2003)), hepatitis B or C virus can lead to liver carcinoma (see, e.g., El-Serag, *J Clin Gastroenterol* 35(5 Suppl 2): S72-8 (2002)), human T cell leukemia virus (HTLV)-I can lead to T-cell leukemia (see e.g., Mortreux et al., *Leukemia* 17(1): 26-38 (2003)), human herpesvirus-8 infection can lead to Kaposi's sarcoma (see, e.g., Kadow et al., *Curr Opin Investig Drugs* 3(11): 1574-9 (2002)), and Human Immunodeficiency Virus (HIV) infection contribute to cancer development as a consequence of immunodeficiency (see, e.g., Dal Maso et al., *Lancet Oncol* 4(2): 110-9 (2003)).

In other embodiments, a subject exhibiting one or more of the following predisposing factors for malignancy can be treated by administration of the present HDACIs and methods of the disclosure: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or procancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, Basic Pathology, 2d Ed., W.B. Saunders Co., Philadelphia, pp. 112-113 (1976)) etc.), and exposure to carcinogens (e.g., smoking, and inhalation of or contacting with certain chemicals).

In another specific embodiment, the present HDACIs and methods of the disclosure are administered to a human subject to prevent progression of breast, colon, ovarian, or cervical cancer.

In one embodiment, the disclosure provides methods for treating cancer comprising (a) administering to an individual in need thereof an amount of a present HDACI; and (b) administering to the individual one or more additional anticancer treatment modality including, but not limited to, radiotherapy, chemotherapy, surgery or immunotherapy, such as a cancer vaccine. In one embodiment, the administering of step (a) is prior to the administering of step (b). In another embodiment, the administering of step (a) is subsequent to the administering of step (b). In still another embodiment, the administering of step (a) is concurrent with the administering of step (b).

In an embodiment, the additional anticancer treatment modality is radiotherapy and/or chemotherapy. In another embodiment, the additional anticancer treatment modality is surgery.

In still another embodiment, the additional anticancer treatment modality is immunotherapy, such as cancer vaccines.

In one embodiment, the immunotherapy comprises anti-PD1 immunotherapy. In another embodiment, the anti-PD1 immunotherapy comprises administration of PD-1 antibody. In another embodiment, the PD-1 antibody is nivolumab, pembrolizumab, STI-A1014, or pidilzumab.

In an embodiment, a present HDACI or a pharmaceutically acceptable salt thereof is administered adjunctively with the additional anticancer treatment modality.

In another embodiment, the additional anticancer treatment modality is radiotherapy. In the methods of the present disclosure, any radiotherapy protocol can be used depending upon the type of cancer to be treated. Embodiments of the present disclosure employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

For example, but not by way of limitation, X-ray radiation can be administered; in some embodiments, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered. Illustrative radiotherapy protocols useful in the present disclosure include, but are not limited to, stereotactic methods where multiple sources of low dose radiation are simultaneously focused into a tissue volume from multiple angles; "internal radiotherapy," such as brachytherapy, interstitial irradiation, and intracavitary irradiation, which involves the placement of radioactive implants directly in a tumor or other target tissue; intraoperative irradiation, in which a large dose of external radiation is directed at the target tissue which is exposed during surgery; and particle beam radiotherapy, which involves the use of fast-moving subatomic particles to treat localized cancers.

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN©, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present HDACI, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

In an embodiment, a present HDACI or a pharmaceutically acceptable salt thereof is administered prior to the administration of radiotherapy and/or chemotherapy.

In another embodiment, a present HDACI or a pharmaceutically acceptable salt thereof is administered adjunctively with radiotherapy and/or chemotherapy.

A present HDACI and additional treatment modalities can act additively or synergistically (i.e., the combination of a present HDACI or a pharmaceutically acceptable salt thereof, and an additional anticancer treatment modality is more effective than their additive effects when each are administered alone). A synergistic combination permits the use of lower dosages of a present HDACI and/or the additional treatment modality and/or less frequent administration of a present HDACI and/or additional treatment modality to a subject with cancer. The ability to utilize lower dosages of a present HDACI and/or an additional treatment modality and/or to administer a compound of the disclosure and the additional treatment modality less frequently can reduce the toxicity associated with the administration without reducing the efficacy of a present HDACI and/or the additional treatment modality in the treatment of cancer. In addition, a synergistic effect can result in the improved efficacy of the treatment of cancer and/or the reduction of adverse or unwanted side effects associated with the administration of a present HDACI and/or an additional anticancer treatment modality as monotherapy.

In an embodiment, the present HDACIs may act synergistically with radiotherapy when administered in doses typically employed when such HDACIs are used alone for the treatment of cancer. In another embodiment, the present HDACIs may act synergistically with radiotherapy when administered in doses that are less than doses typically employed when such HDACIs are used as monotherapy for the treatment of cancer.

In an embodiment, radiotherapy may act synergistically with a present HDACI when administered in doses typically employed when radiotherapy is used as monotherapy for the treatment of cancer. In another embodiment, radiotherapy may act synergistically with a compound of the disclosure when administered in doses that are less than doses typically employed when radiotherapy is used as monotherapy for the treatment of cancer.

The effectiveness of the HDACIs as HDAC inhibitors for sensitizing cancer cells to the effect of radiotherapy can be determined by the in vitro and/or in vivo determination of post-treatment survival using techniques known in the art. In one embodiment, for in vitro determinations, exponentially growing cells can be exposed to known doses of radiation, and the survival of the cells monitored. Irradiated cells are plated and cultured for about 14-about 21 days, and the colonies are stained. The surviving fraction is the number of colonies divided by the plating efficiency of unirradiated cells. Graphing the surviving fraction on a log scale versus the absorbed dose on a linear scale generates a survival curve. Survival curves generally show an exponential decrease in the fraction of surviving cells at higher radiation doses after an initial shoulder region in which the dose is sublethal. A similar protocol can be used for chemical agents when used in the combination therapies of the disclosure.

Inherent radiosensitivity of tumor cells and environmental influences, such as hypoxia and host immunity, can be further assessed by in vivo studies. The growth delay assay is commonly used. This assay measures the time interval required for a tumor exposed to radiation to regrow to a specified volume. The dose required to control about 50% of tumors is determined by the $TCD_{50}$ assay.

In vivo assay systems typically use transplantable solid tumor systems in experimental subjects. Radiation survival parameters for normal tissues as well as for tumors can be assayed using in vivo methods known in the art.

The present disclosure provides methods of treating cancers comprising the administration of an effective amount of a present HDACI in conjunction with recognized methods of surgery, radiotherapy, and chemotherapies, including, for example, chemical-based mimics of radiotherapy whereby a synergistic enhancement of the effectiveness of the recognized therapy is achieved. The effectiveness of a treatment can be measured in clinical studies or in model systems, such as a tumor model in mice, or cell culture sensitivity assays.

The present disclosure provides combination therapies that result in improved effectiveness and/or reduced toxicity. Accordingly, in one aspect, the disclosure relates to the use of the present HDACIs as radiosensitizers in conjunction with radiotherapy.

When the combination therapy of the disclosure comprises administering a present HDACI with one or more additional anticancer agents, the present HDACI and the additional anticancer agents can be administered concurrently or sequentially to an individual. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; anyone or a combination of the additional anticancer agents listed below may be administered.

The present disclosure includes methods for treating cancer comprising administering to an individual in need thereof a present HDACI and one or more additional anticancer agents or pharmaceutically acceptable salts thereof. A present HDACI and the additional anticancer agent can act additively or synergistically. Suitable anticancer agents include, but are not limited to, gemcitabine, capecitabine, methotrexate, taxol, taxotere, and the like.

Additionally, the disclosure provides methods of treatment of cancer using the present HDACIs as an alternative to chemotherapy alone or radiotherapy alone where the chemotherapy or the radiotherapy has proven or can prove too toxic, e.g., results in unacceptable or unbearable side effects, for the subject being treated. The individual being treated can, optionally, be treated with another anticancer treatment modality such as chemotherapy, surgery, or immunotherapy, depending on which treatment is found to be acceptable or bearable.

The present HDACIs can also be used in an in vitro or ex vivo fashion, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of a present HDACI effective to eradicate the subject's remaining bone-marrow cell population, then the stem cell graft is infused back into the subject. Supportive care then is provided while bone marrow function is restored and the subject recovers.

The present methods for treating cancer can further comprise the administration of a present HDACI and an additional therapeutic agent or pharmaceutically acceptable salts or hydrates thereof. In one embodiment, a composition comprising a present HDACI is administered concurrently with the administration of one or more additional therapeutic agent(s), which may be part of the same composition or in a different composition from that comprising the present HDACI. In another embodiment, a present HDACI is administered prior to or subsequent to administration of another therapeutic agent(s).

In the present methods for treating cancer the other therapeutic agent may be an antiemetic agent. Suitable antiemetic agents include, but are not limited to, metoclopromide, domperidone, prochlorperazine, prornethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, and tropisetron. In an embodiment, the antiemetic agent is granisetron or ondansetron. In another embodiment, the other therapeutic agent may be an hematopoietic colony stimulating factor. Suitable hematopoietic colony stimulating factors include, but are not limited to, filgrastim, sargramostim, molgramostim, and epoietin alfa.

In still another embodiment, the other therapeutic agent may be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone, and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, and sulindac.

In still another embodiment, the other therapeutic agent may be an anxiolytic agent. Suitable anxiolytic agents include, but are not limited to, buspirene, and benzodiazepines such as diazepam, lorazepam, oxazapam, chlorazepate, clonazepam, chlordiazepoxide and alprazolam.

In addition to treating cancers and sensitizing a cancer cell to the cytotoxic effects of radiotherapy and chemotherapy, the present HDACIs are used in methods of treating diseases, conditions, and injuries to the central nervous system, such as neurological diseases, neurodegenerative disorders, and traumatic brain injuries (TBIs). In preferred embodiments, a present HDACI is capable of crossing the blood brain barrier to inhibit HDAC in the brain of the individual.

The present HDACI compounds also provide a therapeutic benefit in models of peripheral neuropathies, such as CMT. HDAC6 inhibitors have been found to cross the blood nerve barrier and rescue the phenotype observed in transgenic mice exhibiting symptons of distal hereditary motor neuropathy. Administration of HDAC6 inhibitors to symptomatic mice increased acetylated α-tubulin levels, restored proper mitochondrial motility and axonal transport, and increased muscle re-innervation. Other peripheral neuropathies include, but are not limited to, giant axonal neuropathy and various forms of mononeuropathies, polyneuropathies, autonomic neuropathies, and neuritis.

The present HDACI compounds also ameliorate associative memory loss following Aβ elevation. In this test, mice were infused with Aβ42 via cannulas implanted into dorsal hippocampus 15 minutes prior to training. The test compounds are dosed ip (25 mg/kg) 2 hours before training. Fear learning was assessed 24 hours later.

Contextual fear conditioning performed 24 hours after training shows a reduction of freezing in Aβ-infused mice compared to vehicle-infused mice. Treatment with a present compound ameliorates deficit in freezing responses in AB-infused mice, and has no effect in vehicle-infused mice. A test compound alone does not affect the memory performance of the mice. In addition, treatment had no effects on motor, sensorial, or motivational skills assessed using the visible platform test in which the compounds are injected twice a day for two days. During these experiments, no signs of overt toxicity, including changes in food and liquid intake, weight loss, or changes in locomotion and exploratory behavior, are observed.

These results demonstrate that the HDACIs of the present disclosure are beneficial against impairment of associative memory following Aβ elevation.

The present HDACIs therefore are useful for treating a neurological disease by administration of amounts of a present HDACI effective to treat the neurological disease or by administration of a pharmaceutical composition comprising amounts of a present HDACI effective to treat the neurological disease. The neurological diseases that can be treated include, but are not limited to, Huntington's disease, lupus, schizophrenia, multiple sclerosis, muscular dystrophy, dentatorubralpallidoluysian atrophy (DRRLA), spinal and bulbar muscular atrophy (SBMA), and fine spinocerebellar ataxias (SCA1, SCA2, SCA3/MJD (Machado-Joseph Disease), SCA6, and SCA7), drug-induced movement disorders, Creutzfeldt-Jakob disease, amyotrophic lateral sclerosis, Pick's disease, Alzheimer's disease, Lewy body dementia, cortico basal degeneration, dystonia, myoclonus, Tourette's syndrome, tremor, chorea, restless leg syndrome, Parkinson's disease, Parkinsonian syndromes, anxiety, depression, psychosis, manic depression, Friedreich's ataxia, Fragile X syndrome, spinal muscular dystrophy, Rett syndrome, Rubinstein-Taybi syndrome, Wilson's disease, multi-infarct state, CMT, GAN and other peripheral neuropathies.

In an embodiment, the neurological disease treated is Huntington's disease, Parkinson's disease, Alzheimer's disease, spinal muscular atrophy, lupus, or schizophrenia.

Charcot-Marie-Tooth disease (CMT) is one of the most common inherited neurological disorders that affects about 1 in 2,500 people in the US. CMT affects both motor and sensory nerves which may result in foot drop and a high-stepped gait with frequent tripping or falls. Mutations in the small heat-shock protein 27 (HSPB1) cause axonal CMT or distal hereditary motor neuropathy (distal HMN). Expression of mutant HSPB1 decreased acetylated α-tubulin levels and induced severe axonal transport deficits. Pharmacological inhibition of histone deacetylase 6 (HDAC6)-induced α-tubulin deacetylation caused by HDAC6i Tubastatin A corrects the axonal transport defects induced by HSPB1 mutations and rescues the CMT phenotype of symptomatic mutant HSPB1 mice. The pathogenic role of α-tubulin deacetylation has been demonstrated in mutant HSPB1-induced neuropathies and offers valuable perspectives for HDAC6 inhibitors as a therapeutic strategy for hereditary axonopathies. Compounds of the disclosure show potent HDAC6 isoform inhibition, high HDAC6 selectivity, impressive α-tubulin acetylation in various cell lines.

Accordingly, in another embodiment, the neurological disease is Charcot-Marie-Tooth disease.

A present HDACI also can be used with a second therapeutic agent in methods of treating conditions, diseases, and injuries to the CNS. Such second therapeutic agents are those drugs known in the art to treat a condition, diseases, or injury, for example, but not limited to, lithium in the treatment of mood disorders, estradiol benzoate, and nicotinamide in the treatment of Huntington's disease.

The present HDACIs also are useful in the treatment of TBIs. Traumatic brain injury (TBI) is a serious and complex injury that occurs in approximately 1.4 million people each year in the United States. TBI is associated with a broad spectrum of symptoms and disabilities, including a risk factor for developing neurodegenerative disorders, such as Alzheimer's disease.

TBI produces a number of pathologies including axonal injury, cell death, contusions, and inflammation. The inflammatory cascade is characterized by proinflammatory cytokines and activation of microglia which can exacerbate other pathologies. Although the role of inflammation in TBI is well established, no efficacious anti-inflammatory therapies are currently available for the treatment of TBI.

Several known HDAC inhibitors have been found to be protective in different cellular and animal models of acute and chronic neurodegenerative injury and disease, for example, Alzheimer's disease, ischemic stroke, multiple sclerosis (MS), Huntington's disease (HD), amyotrophic lateral sclerosis (ALS), spinal muscular atrophy (SMA), and spinal and bulbar muscular atrophy (SBMA). A recent study in experimental pediatric TBI reported a decrease in hippocampal CA3 histone H3 acetylation lasting hours to days after injury. These changes were attributed to documented upstream excitotoxic and stress cascades associated with TBI. HDACIs also have been reported to have anti-inflammatory actions acting through acetylation of non-histone proteins. The HDAC6 selective inhibitor, 4-dimethylamino-N-[5-(2-mercaptoacetylamino)pentyl]benzamide (DMA-PB), was found to be able to increase histone H3 acetylation and reduce microglia inflammatory response following traumatic brain injury in rats, which demonstrates the utility of HDACIs as therapeutics for inhibiting neuroinflammation associated with TBI.

The present HDACIs therefore also are useful in the treatment of inflammation and strokes, and in the treatment of autism and autism spectrum disorders. The present HDACIs further can be used to treat parasitic infections, (e.g., malaria, toxoplasmosis, trypanosomiasis, helminthiasis, protozoal infections (see Andrews et al., *Int. J Parasitol.* 30(6): 761-768 (2000)).

The present HDACIs also can be used as imaging agents. In some embodiments, by providing a radiolabeled, isotopically labeled, or fluorescently-labeled HDACI, the labeled compound can image HDACs, tissues expressing HDACs, and tumors. Labeled HDACIs of the present disclosure also can image patients suffering from a cancer, or other HDAC-mediated diseases, e.g., stroke, by administration of an effective amount of the labeled compound or a composition containing the labeled compound. In preferred embodiments, the labeled HDACI is capable of emitting positron radiation and is suitable for use in positron emission tomography (PET). Typically, a labeled HDACI of the present disclosure is used to identify areas of tissues or targets that express high concentrations of HDACs. The extent of accumulation of labeled HDACI can be quantified using known methods for quantifying radioactive emissions. In addition, the labeled HDACI can contain a fluorophore or similar reporter capable of tracking the movement of HDAC isoforms or organelles in vitro.

The present HDACIs useful in the imaging methods contain one or more radioisotopes capable of emitting one or more forms of radiation suitable for detection by any standard radiology equipment, such as PET, SPECT, gamma cameras, MRI, and similar apparatus. Preferred isotopes including tritium ($^{3}H$) and carbon ($^{11}C$). Substituted HDACIs of the present disclosure also can contain isotopes of fluorine ($^{18}F$) and iodine ($^{123}I$) for imaging methods. Typically, a labeled HDACI of the present disclosure contains an alkyl group having a $^{11}C$ label, i.e., a $^{11}C$-methyl group, or an alkyl group substituted with $^{18}F$, $^{123}I$, $^{125}I$, $^{131}I$, or a combination thereof.

Fluorescently-labeled HDACIs of the present disclosure also can be used in the imaging method of the present disclosure. Such compounds have an FITC,carbocyamine moiety or other fluorophore which will allow visualization of the HDAC proteins in vitro.

The labeled HDACIs and methods of use can be in vivo, and on humans, and for in vitro applications, such as diagnostic and research applications, using body fluids and cell samples. Imaging methods using a labeled HDACI of the present disclosure are discussed in WO 03/060523, designating the U.S. and incorporated in its entirety herein. Typically, the method comprises contacting cells or tissues with a radiolabeled, isotopically labeled, fluorescently labeled, or tagged (such as biotin tagged) compound of the disclosure, and making a radiographic, fluorescent, or similar type of image depending on the visualization method employed, i.e., in regared to radiographic images, a sufficient amount to provide about 1 to about 30 mCi of the radiolabeled compound.

Preferred imaging methods include the use of labeled HDACIs of the present disclosure which are capable of generating at least a 2:1 target to background ratio of radiation intensity, or more preferably about a 5:1, about 10:1, or about 15:1 ratio of radiation intensity between target and background.

In preferred methods, the labeled HDACIs of the present disclosure are excreted from tissues of the body quickly to prevent prolonged exposure to the radiation of the radiolabeled compound administered to the individual. Typically, labeled HDACIs of the present disclosure are eliminated from the body in less than about 24 hours. More preferably, labeled HDACIs are eliminated from the body in less than about 16 hours, 12 hours, 8 hours, 6 hours, 4 hours, 2 hours, 90 minutes, or 60 minutes. Typically, preferred labeled HDACIs are eliminated in about 60 to about 120 minutes.

In addition to isotopically labeled and fluorescently labeled derivatives, the present disclosure also embodies the use of derivatives containing tags (such as biotin) for the identification of biomolecules associated with the HDAC isoforms of interest for diagnostic, therapeutic or research purposes.

The present HDACIs also are useful in the treatment of autoimmune diseases and inflammations. Compounds of the present disclosure are useful in overcoming graft and transplant rejections and in treating forms of arthritis.

Despite successes of modern transplant programs, the nephrotoxicity, cardiovascular disease, diabetes, and hyperlipidemia associated with current therapeutic regimens, plus the incidence of post-transplant malignancies and graft loss from chronic rejection, drive efforts to achieve long-term allograft function in association with minimal immunosuppression. Likewise, the incidence of inflammatory bowel disease (IBD), including Crohn's disease and ulcerative colitis, is increasing. Animal studies have shown that T regulatory cells (Tregs) expressing the forkhead transcription family member, Foxp3, are key to limiting autoreactive and alloreactive immunity. Moreover, after their induction by costimulation blockade, immunosuppression, or other strategies, Tregs may be adoptively transferred to naïve hosts to achieve beneficial therapeutic effects. However, attempts to develop sufficient Tregs that maintain their suppressive functions post-transfer in clinical trials have failed. Murine studies show that HDACIs limit immune responses, at least in significant part, by increasing Treg suppressive functions, (Tao et al., *Nat Med* 13: 1299-1307 (2007)), and that selective targeting of HDAC6 is especially efficacious in this regard.

With organ transplantation, rejection begins to develop in the days immediately post-transplant, such that prevention rather than treatment of rejection is a paramount consideration. The reverse applies in autoimmunity, wherein a patient presents with the disease already causing problems. Accordingly, HDAC6−/− mice treated for 14 days with low-dose RPM (rapamycin) are assessed for displaying signs of tolerance induction and resistance to the development of chronic rejection, a continuing major loss of graft function long-term in the clinical transplant population. Tolerance is assessed by testing whether mice with long-surviving allografts reject a subsequent third-party cardiac graft and accept additional donor allografts without any immunosuppression, as can occur using a non-selective HDACI plus RPM. These in vivo sutides are accompanied by assessment of ELISPOT and MLR activities using recipient lymphocytes challenged with donor cells. Protection against chronic rejection is assessed by analysis of host anti-donor humoral responses and analysis of graft transplant arteriosclerosis and interstitial fibrosis in long-surviving allograft recipients.

The importance of HDAC6 targeting is assessed in additional transplant models seeking readouts of biochemical significance, as is monitored clinically. Thus, the effects of HDAC6 in targeting in renal transplant recipients (monitoring BUN, proteinuria) and islet allografts (monitoring blood glucose levels) are assessed. Renal transplants are the most common organ transplants performed, and the kidney performs multiple functions, e.g., regulating acid/base metabolism, blood pressure, red cell production, such that efficacy in this model indicates the utility of HDAC6 targeting. Likewise, islet transplantation is a major unmet need given that clinical islet allografts are typically lost after the first one or two years post-transplant. Having a safe and non-toxic means to extend islet survival without maintenance CNI therapy would be an important advance. Transplant studies also are strengthened by use of mice with floxed HDAC6. Using existing Foxp3-Cre mice, for example, the effects of deletion of HDAC6 just in Tregs is tested. This approach can be extended to targeting of HDAC6 in T cells (CD4-Cre) and dendritic cells (CD11c-Cre), for example. Using tamoxifen-regulated Cre, the importance of HDAC6 in induction vs. maintenance of transplants (with implications for short-term vs. maintenance HDAC6I therapy) is assessed by administering tamoxifen and inducing HDAC6 deletion at varying periods post-transplant.

Studies of autoimmunity also are undertaken. In this case, interruption of existing disease is especially important and HDAC6 targeting can be efficacious without any requirement for additional therapy (in contrast to a need for brief low-dose RPM in the very aggressive, fully MHC-mismatched transplant models). Studies in mice with colitis indicated that HDAC6−/− Tregs were more effective than WT Tregs in regulating disease, and tubacin was able to rescue mice if treatment was begun once colitis had developed. These studies are extended by assessing whether deletion of HDAC6 in Tregs (Foxp3/Cre) vs. T cells (CD4=Cre) vs. DC (CD11c-Cre) differentially affect the development and severity of colitis. Similarly, control of colitis is assessed by inducing HDAC6 deletion at varying intervals after the onset of colitis with tamoxifen-regulated Cre.

The present compounds are envisioned to demonstrate anti-arthritic efficacy in a collagen-induced arthritis model in DBA1/J mice. In this test, DBA1/J mice (male, 7-8 weeks) are used, with 8 animals per group. Systemic arthritis is induced with bovine collagen type II and CFA, plus an IFA booster injection on day 21. A present HDACI is dosed at 50 mg/kg and 100 mg/kg on day 28 for 2 consecutive weeks, and the effects determined from the Average Arthritic Score vs. Days of Treatment data.

Despite efforts to avoid graft rejection through host-donor tissue type matching, in the majority of transplantation procedures, immunosuppressive therapy is critical to the viability of the donor organ in the host. A variety of immunosuppressive agents have been employed in transplantation procedures, including azathioprine, methotrexate, cyclophosphamide, FK-506, rapamycin, and corticosteroids.

The present HDACIs are potent immunosuppressive agents that suppress humoral immunity and cell-mediated immune reactions, such as allograft rejection, delayed hypersensitivity, experimental allergic encephalomyelitis, Freund's adjuvant arthritis and graft versus host disease. HDACIs of the present disclosure are useful for the prophylaxis of organ rejection subsequent to organ transplantation, for treatment of rheumatoid arthritis, for the treatment of psoriasis, and for the treatment of other autoimmune diseases, such as type I diabetes, Crohn's disease, and lupus.

A therapeutically effective amount of a present HDACI can be used for immunosuppression including, for example, to prevent organ rejection or graft vs. host disease, and to treat diseases and conditions, such as, autoimmune and inflammatory diseases and conditions. Examples of autoimmune and inflammatory diseases include, but are not limited to, Hashimoto's thyroiditis, pernicious anemia, Addison's disease, psoriasis, diabetes, rheumatoid arthritis, systemic lupus erythematosus, dermatomyositis, Sjogren's syndrome, dermatomyositis, lupus erythematosus, multiple sclerosis, myasthenia gravis, Reiter's syndrome, arthritis (rheumatoid arthritis, arthritis chronic progrediente, and arthritis deformans) and rheumatic diseases, autoimmune hematological disorder (hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, psoriasis, Steven-Johnson syndrome, idiopathic sprue, autoimmune inflammatory bowel disease (ulcerative colitis and Crohn's disease) endocrine opthalmopathy, Graves disease, sarcoidosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, and glomerulonephritis.

A present HDACI can be used alone, or in conjunction with a second therapeutic agent known to be useful in the treatment of autoimmune diseases, inflammations, transplants, and grafts, such as cyclosporin, rapamycin, methotrexate, cyclophosphamide, azathioprine, corticosteroids, and similar agents known to persons skilled in the art.

Additional diseases and conditions mediated by HDACs, for example, HDAC6, include, but are not limited to asthma, cardiac hypertrophy, giant axonal neuropathy, mononeuropathy, mononeuritis, polyneuropathy, autonomic neuropathy, neuritis in general, and neuropathy in general. These disease and conditions also can be treated by a method of the present disclosure.

In the present method, a therapeutically effective amount of one or more HDACI of the present disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing signs, symptoms and/or malfunctions, and other factors.

A present HDACI can be administered by any suitable route, for example by oral, buccal, inhalation, topical, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a site) administration. Parenteral administration can be accomplished using a needle and syringe or using a high pressure technique.

Pharmaceutical compositions include those wherein a present HDACI is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a present HDACI that is sufficient to maintain therapeutic effects.

Toxicity and therapeutic efficacy of the present HDACI compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such procedures can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present HDACI required for use in therapy varies with the nature of the condition being treated, the length of time that activity is desired, and the age and the condition of the patient, and ultimately is determined by the attendant physician. Dosage amounts and intervals can be adjusted individually to provide plasma levels of the HDACI that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present HDACI can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a present HDACI, or a composition containing the same, can be from about 1 ng/kg to about 200 mg/kg, about 1 μg/kg to about 100 mg/kg, or about 1 mg/kg to about 50 mg/kg of body weight. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the patient.

A present HDACI used in a method of the present disclosure typically is administered in an amount of about 0.005 to about 500 milligrams per dose, about 0.05 to about 250 milligrams per dose, or about 0.5 to about 100 milligrams per dose. For example, a present HDACI can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The HDACIs of the present disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and auxiliaries that facilitate processing of the present HDACIs.

The term "carrier" refers to a diluent, adjuvant, or excipient, with which a present HDACI is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when a present HDACI is administered intravenously. Saline solutions and aqueous dextrose and glycerol solutions can also be employed as liquid carriers, for example, for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a present HDACI is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present HDACI. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present compound.

When a therapeutically effective amount of a present HDACI is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains an isotonic vehicle. A present HDACI can be infused with other fluids over a 10-30 minute span or over several hours.

The present HDACIs can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present HDACI to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present HDACI can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present HDACI can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present HDACI also can be formulated in rectal compositions, such as suppositories or retention enemas, e.g., containing conventional suppository bases. In addition to the formulations described previously, a present HDACI also can be formulated as a depot preparation. Such long-acting formulations can be administered by implantation (for example, subcutaneously or intramuscularly) or by intramuscular injection. Thus, for example, a present HDACI can be formulated with suitable polymeric or hydrophobic materials (for example, as an emulsion in an acceptable oil) or ion exchange resins.

In some embodiments, a present HDACI can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The present HDACIs also can be injected parenterally, for example, intravenously, intramuscularly, subcutaneously, or intracoronarily. For parenteral administration, the present HDACIs are best used in the form of a sterile aqueous solution which can contain other substances, for example, salts or monosaccharides, such as mannitol or glucose, to make the solution isotonic with blood.

As an additional embodiment, the present disclosure includes kits which comprise one or more compounds or compositions packaged in a manner that facilitates their use to practice methods of the disclosure. In one simple embodiment, the kit includes a compound or composition described herein as useful for practice of a method (e.g., a composition comprising a present HDACI and an optional second therapeutic agent), packaged in a container, such as a sealed bottle or vessel, with a label affixed to the container or included in the kit that describes use of the compound or composition to practice the method of the disclosure. Preferably, the compound or composition is packaged in a unit dosage form. The kit further can include a device suitable for administering the composition according to the intended route of administration, for example, a syringe, drip bag, or patch. In another embodiment, the present compounds is a lyophilate. In this instance, the kit can further comprise an additional container which contains a solution useful for the reconstruction of the lyophilate.

Prior HDACIs possessed properties that hindered their development as therapeutic agents. In accordance with an important feature of the present disclosure, the present HDACIs were synthesized and evaluated as inhibitors for HDAC. The present compounds demonstrate an increased HDAC6 potency and selectivity against HDAC1 and HDAC8 with improvements in BEI relative to prior compounds. The improved properties of the present compounds, for example, the increase in BEI and reduced potency at HDAC8, indicate that the present compounds are useful for applications such as, but not limited to, immunosuppresssive and neuroprotective agents. For example, compounds of the present disclosure typically have a bonding affinity ($IC_{50}$) to HDAC6 of less than 100 μM, less than 25 μM, less than 10 μM, less than 1 μM, less than 0.5 μM, and less than 0.2 μM.

Synthetic Methods and Procedures

All starting materials and solvents were purchased from commercial suppliers at reagent purity and, unless otherwise noted, were used as obtained without any further purification. Dry solvents used as media in moisture-sensitive reactions were purchased from Sigma-Aldrich at anhydrous grade and handled under argon. All reactions were carried out in dry conditions, under inert (argon) atmosphere. Microwave reactions were run in a Biotage Initiator microwave reactor. Reactions were monitored by thin layer chromatography on silica gel-coated glass plates (TLC LuxPlate Silica gel 60 $F_{254}$, Merck), with visualization at 254 nm, and/or using appropriate dyes. Where indicated, synthetic intermediates were purified by 230-400 mesh silica gel flash chromatography on a CombiFlash system, using appropriate solvent mixtures. Final products were purified by preparative HPLC using a Shimadzu preparative liquid chromatograph [ACE 5AQ (150×21.2 mm) with 5 μm particle size. Method 1: 25-100% MeOH/$H_2O$, 30 min; 100% MeOH, 5 min; 100-25% MeOH/$H_2O$, 4 min. Method 2: 8-100% MeOH/$H_2O$, 30 min; 100% MeOH, 5 min; 100-8% MeOH/$H_2O$, 4 min. Method 3: 0% MeOH, 5 min; 0-100% MeOH/$H_2O$, 25 min; 100% MeOH, 5 min; 100-0% MeOH/$H_2O$, 4 min. Flow rate=17 mL/min], with monitoring at 254 and 280 nm. Both solvents were spiked with 0.05% TFA. $^{1}H$ and $^{13}C$ NMR spectra were recorded at 400 MHz and 100.6 MHz, respectively, on Bruker DPX-400 or AVANCE-400 spectrometers. Chemical shifts (S scale) are reported in parts per million (ppm) relative to TMS. $^{1}H$ NMR spectra are reported in this order: multiplicity and number of protons; signals were characterized as: s (singlet), d (doublet), dd (doublet of doublets), t (triplet), m (multiplet), bs (broad signal). HRMS spectra were recorded using ESI with an LCMS-IT-TOF (Shimadzu). Purity of all final compounds was determined by analytical HPLC [ACE 3AQ C18 column (150×4.6 mm, particle size 3 μM); 0.05% TFA in $H_2O$/0.05% TFA in MeOH gradient eluting system; flow rate=1.0 mL/min]. All compounds were tested at >95% purity as determined by HPLC analysis.

The synthetic route to Suprastat, a representative HDAC6 inhibitor of the disclosure, is shown in Scheme 1. According to Scheme 1, a general carbamate intermediate 2 from phenyl chloroformate and aniline 1 under $K_2CO_3$/acetone conditions. Methyl 4-formylbenzoate 3a underwent a rapid reductive amination with 4-amino-1-butanol to provide intermediate 4a. Subsequently, the combination reaction between 2 and 4a under TEA/TIF conditions afforded the key urea precursor 5a, which further converted to the final hydroxamate product 6a (Suprastat) using aqueous hydroxylamine under basic conditions and using TFA/TIF conditions to deprotect Boc group. To evaluate together with Suprastat in the following biological experiments, analog 6b bearing aminomethyl group and original butyl chain attached to the proximal urea nitrogen was also prepared using the same synthetic route to Suprastat. The synthesis of 6c (Table 1), which contains a hydroxylbutyl side chain, has been previously reported (see, e.g., Bergman et al., *J. Med. Chem.* 55: 9891-9899 (2012)). Moreover, non-hydroxamate analogs 6d-f containing the same cap with Supratstat were prepared and evaluated to explore if additional hydrogen binding interactions would be able to retain activity without a hydroxamate ZBG, inspired by ketone/amide-based Class I HDACIs (see, e.g., Koya et al., *Cancer Res.* 72: 3928-3937 (2012); or O'Donnell et al., *Cancer Treat Rev.* 52: 71-81 (2017)). The carboxylic acid analog 6d was directly afforded from the urea ester 5a through hydrolysis under basic condition and Boc deprotection. To synthesize the amide analog 6e, 4-formylbenzonitrile 3b underwent the two-step reductive amination followed by the reaction with carbamate 2 to generate the intermediate urea 5c. The nitrile group in 5c was further converted to an amide group by treating with aqueous hydrogen peroxide solution under basic condition, and the final product 6e was afforded through Boc deprotection as described above. The synthetic route to the boronic acid analog 6f initiated with the reductive amination of 4-bromobenzaldehyde 3c followed by urea formation using the same procedures as above to give the intermediate urea 5d. The precursor 5d underwent coupling reaction with bis(pinacolato)diboron under KOAc/Pd(dppf)$Cl_2$ conditions. In the end, the desired boronic acid product 6f was obtained through pinacol deprotection and Boc deprotection under $NaIO_4$/$NH_4OAc$ and TFA/THF, respectively.

Scheme 1

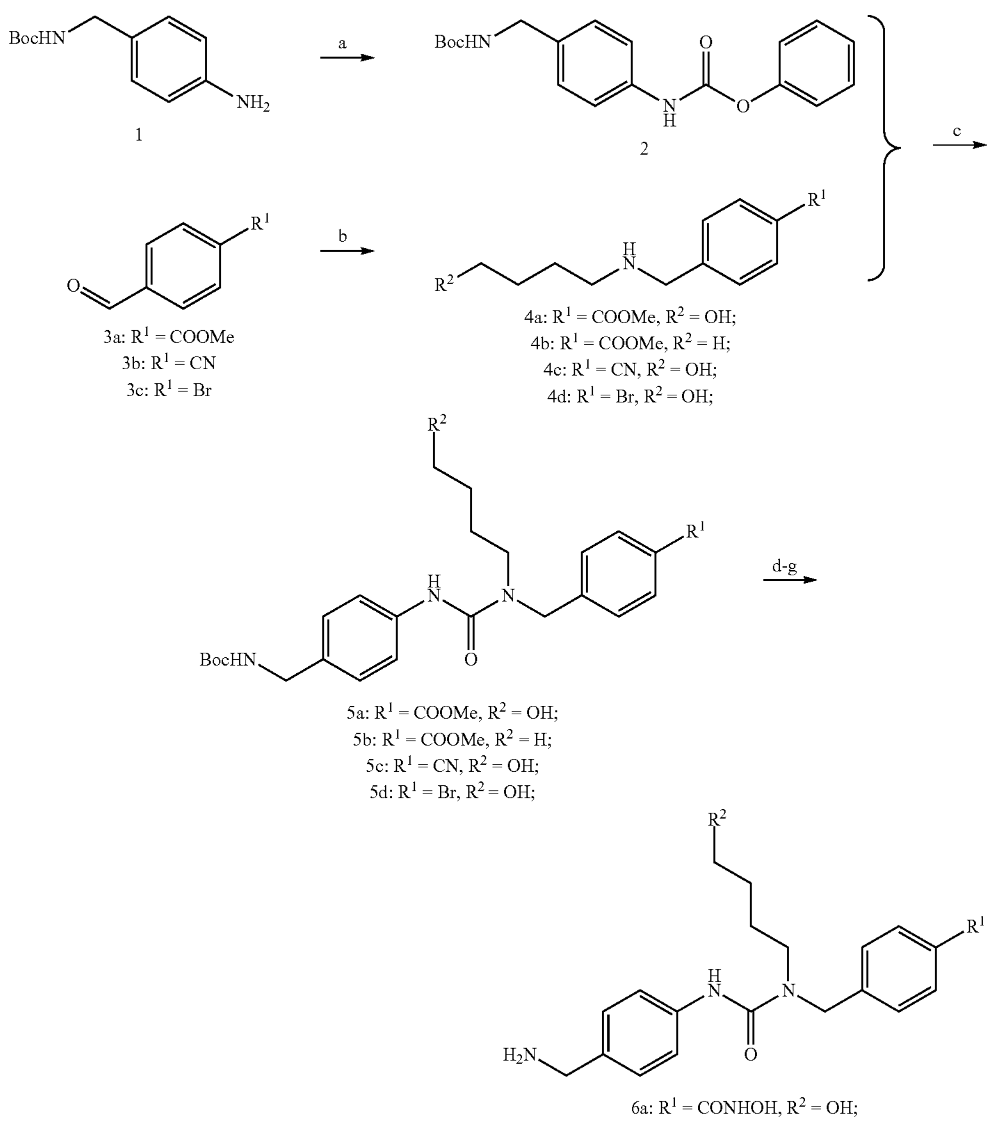

1

2

3a: $R^1$ = COOMe
3b: $R^1$ = CN
3c: $R^1$ = Br

4a: $R^1$ = COOMe, $R^2$ = OH;
4b: $R^1$ = COOMe, $R^2$ = H;
4c: $R^1$ = CN, $R^2$ = OH;
4d: $R^1$ = Br, $R^2$ = OH;

5a: $R^1$ = COOMe, $R^2$ = OH;
5b: $R^1$ = COOMe, $R^2$ = H;
5c: $R^1$ = CN, $R^2$ = OH;
5d: $R^1$ = Br, $R^2$ = OH;

6a: $R^1$ = CONHOH, $R^2$ = OH;
6b: $R^1$ = CONHOH, $R^2$ = H;
6d: $R^1$ = COOH, $R^2$ = OH;
6e: $R^1$ = $CONH_2$, $R^2$ = OH;
6f: $R^1$ = $B(OH)_2$, $R^2$ = OH;

Scheme 1 Synthetic route to 6a-b. Reagents and conditions: (a) phenyl chloroformate, $K_2CO_3$, acetone, rt, 2 h; (b) i) 4-amino-1-butanol for 4a, 4c, and 4d and n-butylamine for 4b, EtOH, reflux, 2 h; ii) $NaBH_4$, MeOH, 0° C. - rt, 2 h; (c) 2, TEA, THF, reflux, 2 h; (d) for 6a and 6b: i) aq. $NH_2OH$ (50%), NaOH, THF/MeOH, 0° C., 15 min; ii) TFA, THF, rt, 0.5 h; (e) for 6d: i) 1N NaOH, THF/MeOH, rt, overnight; ii) TFA, THF, rt, 0.5 h; (f) for 6e: i) $H_2O_2$ (30%), $K_2CO_3$, DMSO, rt, 5 h; ii) TFA, THF, rt, 0.5 h; (g) for 6f: i) $B_2pin_2$, KOAc, $Pd(dppf)Cl_2$, DMF, 80° C., overnight; ii) $NaIO_4$, $NH_4OAc$, acetone-$H_2O$, rt, overnight; iii) TFA, THF, rt, 0.5 h.

Use of the HDAC Inhibitors

An HDACI of the present disclosure can be used alone, or in conjunction with a second therapeutic agent known to be useful in the treatment of various diseases including autoimmune diseases, inflammations, transplants, and grafts, such as cyclosporin, rapamycin, methotrexate, cyclophosphamide, azathioprine, corticosteroids, and similar agents known to persons skilled in the art.

Additional diseases and conditions mediated by HDACs, and for example, HDAC6, include, but are not limited to asthma, cardiac hypertrophy, giant axonal neuropathy, mononeuropathy, mononeuritis, polyneuropathy, autonomic neuropathy, neuritis in general, and neuropathy in general. These disease and conditions also can be treated by a method of the present disclosure.

In the present method, a therapeutically effective amount of one or more HDACI of the present disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing signs, symptoms and/or malfunctions, and other factors.

A present HDACI can be administered by any suitable route, for example by oral, buccal, inhalation, topical, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a site) administration. Parenteral administration can be accomplished using a needle and syringe or using a high pressure technique.

Pharmaceutical compositions include those wherein a present HDACI is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a present HDACI that is sufficient to maintain therapeutic effects.

Toxicity and therapeutic efficacy of the present HDACI compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such procedures can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present HDACI required for use in therapy varies with the nature of the condition being treated, the length of time that activity is desired, and the age and the condition of the patient, and ultimately is determined by the attendant physician. Dosage amounts and intervals can be adjusted individually to provide plasma levels of the HDACI that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present HDACI can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3) five daily doses, with two days rest, and another five daily doses (5/2/5); or, any dose regimen determined to be appropriate for the circumstance.

The dosage of a composition containing a present HDACI, or a composition containing the same, can be from about 1 ng/kg to about 200 mg/kg, about 1 μg/kg to about 100 mg/kg, or about 1 mg/kg to about 50 mg/kg of body weight. The dosage of a composition may be at any dosage including, but not limited to, about 1 μg/kg, 10 μg/kg to 200 mg/kg. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the patient.

A present HDACI used in a method of the present disclosure typically is administered in an amount of about 0.005 to about 500 milligrams per dose, about 0.05 to about 250 milligrams per dose, or about 0.5 to about 100 milligrams per dose. For example, a present HDACI can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The HDACIs of the present disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and auxiliaries that facilitate processing of the present HDACIs.

The term "carrier" refers to a diluent, adjuvant, or excipient, with which a present HDACI is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when a present HDACI is administered intravenously. Saline solutions and aqueous dextrose and glycerol solutions can also be employed as liquid carriers, for example, for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a present HDACI is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present HDACI. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present compound.

When a therapeutically effective amount of a present HDACI is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains an isotonic vehicle. A present HDACI can be infused with other fluids over a 10-30 minute span or over several hours.

The present HDACIs can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present HDACI to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present HDACI can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present HDACI can be prepared as appropriate oily injection suspensions. Suitable lipophilic solvents or vehicles include fatty oils or synthetic fatty acid esters. Aqueous injection suspensions can contain substances which increase the viscosity of the suspension.

Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present HDACI also can be formulated in rectal compositions, such as suppositories or retention enemas, e.g., containing conventional suppository bases. In addition to the formulations described previously, a present HDACI also can be formulated as a depot preparation. Such long-acting formulations can be administered by implantation (for example, subcutaneously or intramuscularly) or by intramuscular injection. Thus, for example, a present HDACI can be formulated with suitable polymeric or hydrophobic materials (for example, as an emulsion in an acceptable oil) or ion exchange resins.

In some embodiments, a present HDACI can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The present HDACIs also can be injected parenterally, for example, intravenously, intramuscularly, subcutaneously, or intracoronarily. For parenteral administration, the present HDACIs are best used in the form of a sterile aqueous solution which can contain other substances, for example, salts or monosaccharides, such as mannitol or glucose, to make the solution isotonic with blood.

As an additional embodiment, the present disclosure includes kits which comprise one or more compounds or compositions packaged in a manner that facilitates their use to practice methods of the disclosure. In one simple embodiment, the kit includes a compound or composition described herein as useful for practice of a method (e.g., a composition comprising a present HDACI and an optional second therapeutic agent), packaged in a container, such as a sealed bottle or vessel, with a label affixed to the container or included in the kit that describes use of the compound or composition to practice the method of the disclosure. Preferably, the compound or composition is packaged in a unit dosage form. The kit further can include a device suitable for administering the composition according to the intended route of administration, for example, a syringe, drip bag, or patch. In another embodiment, the selected compound is a lyophilate. In this instance, the kit can further comprise an additional container which contains a solution useful for the reconstruction of the lyophilate.

A number of the prior HDACIs possess properties that are likely to hinder their development as therapeutic agents for diseases other than cancer due to the fact that they often show activity against a number of the known HDACs. Accordingly, an important feature of the present disclosure relates to the fact that compounds of the present disclosure show isoform selectivity. The present compounds demonstrate an increased inhibitory potency and selectivity for HDAC6 relative to other HDACs, for example, greater selectivity for Class II over Class I. The improved properties of the present compounds indicate that these compounds should be useful for applications such as, but not limited to immunosuppresssive and neuroprotective agents, as well as Alzheimer's disease, depression, Rett syndrome, Charcot Marie Tooth disease, brain cancer, and others. For example, compounds of the present disclosure typically have a bonding affinity ($IC_{50}$) to HDAC6 of less than 1 μM, and in some cases less than 10 nM.

In some aspects, the disclosure provides the following particular embodiments.

Embodiment 1. A compound of Formula I, as above, or a pharmaceutically acceptable salt thereof, wherein $R^1$ and $R^2$ are independently selected from the group consisting of hydrogen and $C_1$-$C_6$ alkyl, or $R^1$ and $R^2$ are joined to form a 3-7 membered heterocyclyl; $L^1$ is $CO_2H$, $C(O)NH_2$, C(O)NHOH, or $B(OH)_2$; $L^2$ is H or $OR^3$; $R^3$ is selected from the group consisting of hydrogen, acetyl, $C_1$-$C_6$ alkyl, $C_1$-$C_6$ haloalkyl, $C_3$-$C_6$cycloalkyl, aryl, heteroaryl, and $C_5$-$C_6$ heterocyclyl; each X is independently hydrogen or halogen; p is 0, 1, 2, or 3; Y and Z are independently selected from the group consisting of carbon and nitrogen; m is 1, 2, 3 or 4; and n is 0, 1 or 2.

Embodiment 2. The compound of Embodiment 1, or a pharmaceutically acceptable salt thereof, wherein $R^1$, $R^2$ and $R^3$ are independently $C_1$-$C_6$ branched alkyl.

Embodiment 3. The compound of Embodiment 1, or a pharmaceutically acceptable salt thereof, wherein $L^1$ is C(O)NHOH.

Embodiment 4. The compound of Embodiment 1, or a pharmaceutically acceptable salt thereof, wherein the compound is Formula Ib.

Embodiment 5. The compound of Embodiment 1, or a pharmaceutically acceptable salt thereof, wherein the compound is Formula Ic.

Embodiment 6. The compound of Embodiment 1, or a pharmaceutically acceptable salt thereof, wherein the compound is Formula Id.

Embodiment 7. The compound of Embodiment 1, or a pharmaceutically acceptable salt thereof, wherein the compound is Formula Ie.

Embodiment 8. The compound of Embodiment 1, or a pharmaceutically acceptable salt thereof, wherein the compound is compound 6a, 6b, 6d, 6e, or 6f.

Embodiment 9. A composition comprising (a) the compound of any one of Formulae I, Ib, Ic, Id, or Ie, or compound 6a, 6b, 6d, 6e, or 6f, (b) a second therapeutic agent useful in the treatment of a disease or condition wherein inhibition of HDAC provides a benefit, and (c) an optional excipient and/or pharmaceutically acceptable carrier.

Embodiment 10. The composition of Embodiment 9 wherein the second therapeutic agent comprises a chemotherapeutic agent useful in the treatment of a cancer.

Embodiment 11. A pharmaceutical composition comprising the compound of any one of Formulae I, Ib, Ic, Id, or Ie, or compound 6a, 6b, 6d, 6e, or 6f, and a pharmaceutically acceptable carrier or vehicle.

Embodiment 12. Use of the compound of any one of Formulae I, Ib, Ic, Id, or Ie, or compound 6a, 6b, 6d, 6e, or 6f, for the manufacture of a medicament for treating a disease or condition in an individual wherein the inhibition of HDAC provides a benefit.

Embodiment 13. The use of Embodiment 12 wherein the HDAC is HDAC6.

Embodiment 14. The use of Embodiment 12 further comprising administering a therapeutically effective amount of a second therapeutic agent useful in the treatment of the disease or condition.

Embodiment 15. The use of Embodiment 12 wherein the compound of any one of Formulae I, Ib, Ic, Id, or Ie, or compound 6a, 6b, 6d, 6e, or 6f, and the second therapeutic agent are administered simultaneously.

Embodiment 16. The use of Embodiment 12 wherein the compound of any one of Formulae I, Ib, Ic, Id, or Ie, or compound 6a, 6b, 6d, 6e, or 6f, and the second therapeutic agent are administered separately.

Embodiment 17. The use of any one of Embodiments 12-16 wherein the disease or condition is a cancer.

Embodiment 18. The use of any one of Embodiments 12-17 wherein the disease is a cancer and the second therapeutic agent is one or more of a chemotherapeutic agent, radiation, and an immunotherapy.

Embodiment 19. The use of Embodiment 18 wherein the immunotherapy comprises anti-PD1 immunotherapy.

Embodiment 20. The use of Embodiment 19 wherein the anti-PD1 immunotherapy comprises administration of a PD-1 antibody.

Embodiment 21. The use of Embodiment 20 wherein the PD-1 antibody is nivolumab, pembrolizumab, STI-A1014, or pidilzumab.

Embodiment 22. The use of any one of Embodiments 14-21 wherein the second therapeutic agent comprises radiation, and the radiation optionally is administered in conjunction with radiosensitizers and/or therapeutic agents.

Embodiment 23. The use of any one of Embodiments 12-22 wherein the disease or condition is a neurological disease, a neurodegenerative disorder, peripheral neuropathy, or a traumatic brain injury.

Embodiment 24. The use of any one of Embodiments 12-23 wherein the disease or condition is a stroke.

Embodiment 25. The use of any one of Embodiment 12-24 wherein the disease or condition is an inflammation or an autoimmune disease.

Embodiment 26. The use of Embodiment 25 further comprising administering a therapeutically effective amount of a second therapeutic agent useful in the treatment of the autoimmune disease or the inflammation.

Embodiment 27. Use of the compound of any one of Formulae I, Ib, Ic, Id, or Ie, or compound 6a, 6b, 6d, 6e, or 6f, for increasing sensitivity of a cancer cell to cytotoxic effects of a radiotherapy and/or a chemotherapy.

Embodiment 28. A kit comprising the compound of any one of Formulae I, Ib, Ic, Id, or Ie, or compound 6a, 6b, 6d, 6e, or 6f, and instructions for administering the compound, or a pharmaceutically acceptable salt thereof, to a subject in need thereof.

Embodiment 29. The kit of Embodiment 28 wherein the subject has cancer.

Embodiment 30. The kit of Embodiment 29 further comprising an anti-PD1 antibody.

Embodiment 31. A compound of any one of Formulae I, Ib, Ic, Id, or Ie, or compound 6a, 6b, 6d, 6e, or 6f, for use in treating a disease or condition in an individual wherein the inhibition of HDAC provides a benefit.

Embodiment 32. The compound for use of Embodiment 31 wherein the HDAC is HDAC6.

Embodiment 33. The compound for use of Embodiment 31 further comprising administering a therapeutically effective amount of a second therapeutic agent useful in the treatment of the disease or condition.

Embodiment 34. The compound for use of Embodiment 31 wherein the compound of any one of Formulae I, Ib, Ic, Id, or Ie, or compound 6a, 6b, 6d, 6e, or 6f, and the second therapeutic agent are administered simultaneously Embodiment 35. The compound for use of Embodiment 31 wherein the compound of any one of Formulae I, Ib, Ic, Id, or Ie, or compound 6a, 6b, 6d, 6e, or 6f, and the second therapeutic agent are administered separately.

Embodiment 36. The compound for use of any one of Embodiments 31-35 wherein the disease or condition is a cancer.

Embodiment 37. The compound for use of any one of Embodiments 31-36 wherein the disease is a cancer and the second therapeutic agent is one or more of a chemotherapeutic agent, radiation, and an immunotherapy.

Embodiment 38. The compound for use of Embodiments 37 wherein the immunotherapy comprises anti-PD1 immunotherapy.

Embodiment 39. The compound for use of Embodiments 38 wherein the anti-PD1 immunotherapy comprises administration of PD-1 antibody.

Embodiment 40. The compound for use of Embodiments 39 wherein the PD-1 antibody is nivolumab, pembrolizumab, STI-A1014, or pidilzumab.

Embodiment 41. The compound for use of any one of Embodiments 33-40 wherein the second therapeutic agent comprises radiation, and the radiation optionally is administered in conjunction with radiosensitizers and/or therapeutic agents.

Embodiment 42. The compound for use of any one of Embodiments 31-41 wherein the disease or condition is a neurological disease, a neurodegenerative disorder, peripheral neuropathy, or a traumatic brain injury.

Embodiment 43. The compound for use of any one of Embodiments 31-42 wherein the disease or condition is a stroke.

Embodiment 44. The compound for use of any one of Embodiments 31-43 wherein the disease or condition is an inflammation or an autoimmune disease.

Embodiment 45. The compound for use of Embodiment 44 further comprising administering a therapeutically effective amount of a second therapeutic agent useful in the treatment of the autoimmune disease or the inflammation.

Embodiment 46. A compound of any one of Formulae I, Ib, Ic, Id, or Ie, or compound 6a, 6b, 6d, 6e, or 6f, for use of increasing sensitivity of a cancer cell to cytotoxic effects of a radiotherapy and/or a chemotherapy.

The foregoing may be better understood by reference to the following Examples, which are presented for purposes of illustration and are not intended to limit the scope of the disclosure.

EXAMPLES

General Information $^1H$ and $^{13}C$ NMR spectra were obtained on 400/101 and 500/126 MHz Bruker spectrometers, except where noted otherwise, using the solvent residual peak as the internal reference (chemical shifts: $CDCl_3$, δ 7.26/77.16 and DMSO-$d_6$, 2.50/39.52). The following abbreviations for multiplicities were used: s=singlet, d=doublet, t=triplet, q=quartet, m=multiplet, and br s=broad singlet. TLC plates (Merck silica gel 60 $F_{254}$, 250 m thickness) were used to monitor reaction progress, and spots were visualized under UV (254 nm). High-resolution mass spectrometry (HIRMS) was carried out on a Shimadzu IT-TOF instrument under the following conditions: column, ACE 3AQ (50×2.1 mm, id); mobile phase, 5-100% acetonitrile/water containing 0.1% formic acid at a flow rate of 0.5 mL/min for 4 min. Flash chromatography was performed on a Combi-Flash Rf system (Teledyne ISCO) with silica gel cartridges. Preparative HPLC was used in the purification of all final compounds using a Shimadzu preparative LC under the following conditions: column, ACE 5AQ (150×21.2 mm, id); mobile phase: 5-100% acetonitrile/water containing 0.05% TFA at a flow rate of 17 mL/min for 30 min; UV detection at 254 and 280 nm. Analytical HPLC was carried out on an Agilent 1260 series instrument under the following conditions: column, ACE 3 (150×4.6 mm, id); mobile phase, 5-100% acetonitrile/water containing 0.05% TFA at a flow rate of 1.0 mL/min for 25 min; UV detection at 254 nm. The purity of all tested compounds for in vitro biological studies was >95%. The purity of Suprastat for crystallographic and in vivo studies was >98%.

2

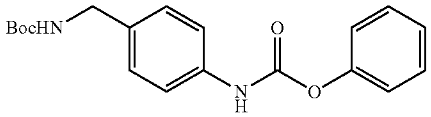

Phenyl (4-(((tert-Butoxycarbonyl)amino)methyl)phenyl) carbamate (2). To a stirred solution of tert-butyl (4-aminobenzyl)carbamate (1, 500 mg, 2.25 mmol) and $K_2CO_3$ (373 mg, 2.70 mmol) in acetone (15 mL) was added phenyl chloroformate (352 mg, 2.25 mmol) over 10 min. After stirring at room temperature for 2 h, the excess solid was filtered off. The filtrate was collected and concentrated under vacuum. The crude product was purified via flash chromatography (0-50% EtOAc/hexane) to afford 2 as a light yellow solid (700 mg, yield: 91%). $^1H$ NMR (400 MHz, $CDCl_3$) δ 7.41-7.37 (m, 4H), 7.25-7.16 (m, 6H), 4.86 (s, 1H), 4.27 (d, J=4.7 Hz, 2H), 1.46 (s, 9H). $^{13}C$ NMR (101 MHz, $CDCl_3$) δ 156.1, 151.8, 150.7, 136.8, 134.6, 129.5 (2C), 128.4 (2C), 125.8, 121.8 (2C), 119.1 (2C), 79.7, 44.3, 28.5 (3C).

4a

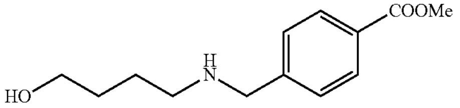

Methyl 4-(((4-Hydroxybutyl)amino)methyl)benzoate (4a). (i) A solution of 4-amino-1-butanol (0.28 mL, 6.10 mmol) and methyl-4-formylbenzoate (3a, 500 mg, 3.05 mmol) in EtOH (25 mL) was heated to reflux for 2 h. After cooling to room temperature, the resulting mixture was concentrated, and the crude product was used directly to next step. (ii) To a stirred solution of the crude product in MeOH (50 mL), sodium borohydride (116 mg, 3.10 mmol) was added over 10 min at 0° C. The resulting mixture was allowed to warm to room temperature and stirred at room temperature for 2 h. Then the reaction was quenched with water and extracted with EtOAc (15 mL×3). The combined organic layers were washed with brine, dried over $Na_2SO_4$, and concentrated under vacuum to afford 4a as a colorless oil. The product was used directly in next step without further purification (630 mg, yield: 87% over two steps). $^1H$ NMR (400 MHz, $CDCl_3$) δ 7.98 (d, J=8.1 Hz, 2H), 7.36 (d, J=8.0 Hz, 2H), 3.88 (s, 3H), 3.82 (s, 2H), 3.58 (t, J=5.0 Hz, 2H), 3.07 (br s, 2H, NH+OH), 2.67 (t, J=5.4 Hz, 2H), 1.71-1.53 (m, 4H). $^{13}C$ NMR (101 MHz, $CDCl_3$) δ 167.0, 144.6, 130.0 (2C), 129.2, 128.3 (2C), 62.7, 53.6, 52.2, 49.4, 32.2, 28.4.

4b

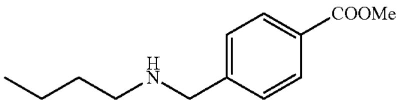

Methyl 4-((Butylamino)methyl)benzoate (4b) was synthesized from n-butylamine (0.31 mL, 6.10 mmol) and methyl-4-formylbenzoate (3a, 500 mg, 3.05 mmol) using a procedure similar to that described for the synthesis of 4a and was obtained as a colorless oil (500 mg, yield: 74% over two steps. $^1H$ NMR (400 MHz, $CDCl_3$) δ 7.99 (d, J=8.3 Hz, 2H), 7.39 (d, J=8.3 Hz, 2H), 3.90 (s, 3H), 3.84 (s, 2H), 2.75-2.51 (m, 2H), 1.53-1.45 (m, 2H), 1.39-1.30 (m, 2H), 0.91 (t, J=7.3 Hz, 3H). $^{13}C$ NMR (101 MHz, $CDCl_3$) δ 166.7, 145.9, 129.5 (2C), 128.5, 127.7 (2C), 53.5, 51.7, 49.0, 32.1, 20.3, 13.8.

4c

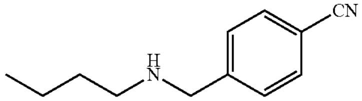

4-(((4-Hydroxybutyl)amino)methyl)benzonitrile (4c) was synthesized from 4-amino-1-butanol (0.10 mL, 1.0 mmol) and 4-formylbenzonitrile (3b, 131 mg, 1.0 mmol) using a procedure similar to that described for the synthesis of 4a and was obtained as a colorless oil (120 mg, yield: 59% over two steps).

4c

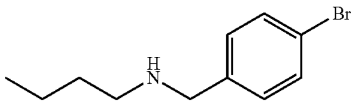

4-((4-Bromobenzyl)amino)butan-1-ol (4d) was synthesized from 4-amino-1-butanol (0.276 mL, 3 mmol) and 4-bromobenzaldehyde (3c, 550 mg, 3 mmol) using a procedure similar to that described for the synthesis of 4a and was obtained as a colorless oil (0.53 g, yield: 68% over two steps).

5a

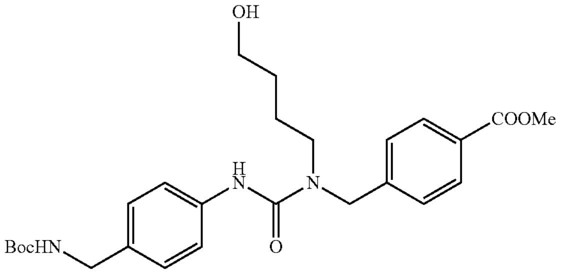

Methyl 4-((3-(4-(((tert-Butoxycarbonyl)amino)methyl)phenyl)-1-(4-hydroxybutyl)-ureido)methyl)-benzoate (5a). To a stirred solution of 4a (284 mg, 1.2 mmol) and 2 (350 mg, 1.0 mmol) in THF (10 mL) was added TEA (0.28 mL, 2.0 mmol). The resulting mixture was heated to reflux for 2 h. Then the reaction was cooled to room temperature, quenched with water (10 mL), and extracted with EtOAc (10 mL×3). The combined organic layers were washed with brine, dried over $Na_2SO_4$, and concentrated under vacuum. The residue was purified via flash chromatography (0-50% EtOAc/hexane) to afford 5a as a colorless oil (420 mg, yield: 87%). $^1$H NMR (400 MHz, $CDCl_3$) δ 7.94 (d, J=8.1 Hz, 2H), 7.65 (br s, 1H), 7.29 (d, J=8.1 Hz, 4H), 7.05 (d, J=8.1 Hz, 2H), 5.10 (br s, 1H), 4.56 (s, 2H), 4.14 (s, 2H), 3.87 (s, 3H), 3.65 (d, J=4.9 Hz, 2H), 3.53 (br s, 1H, —OH), 3.31 (d, J=6.2 Hz, 2H), 1.64 (s, 2H), 1.53-1.45 (m, 2H), 1.40 (s, 9H). $^{13}$C NMR (101 MHz, $CDCl_3$) δ 167.0, 156.2, 156.1, 143.7, 138.7, 133.2, 130.0 (2C), 129.2, 127.8 (2C), 127.3 (2C), 120.3 (2C), 79.5, 62.5, 52.2, 49.9, 46.9, 44.1, 28.4 (3C), 27.6, 25.4.

5b

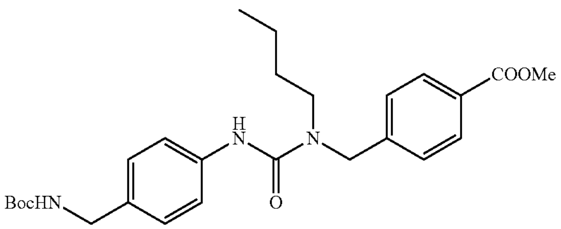

Methyl 4-((3-(4-(((tert-Butoxycarbonyl)amino)methyl)phenyl)-1-butylureido)-methyl)benzoate (5b) was synthesized from 4b (265 mg, 1.2 mmol) and 2 (350 mg, 1.0 mmol) using a procedure similar to that described for the synthesis of 5a and was obtained as a colorless oil (400 mg, yield: 85%). $^1$H NMR (400 MHz, $CDCl_3$) δ 7.98 (d, J=8.2 Hz, 2H), 7.33 (d, J=8.1 Hz, 2H), 7.24 (d, J=8.4 Hz, 2H), 7.12 (d, J=8.0 Hz, 2H), 6.52 (d, J=6.6 Hz, 1H), 4.92 (s, 1H), 4.60 (s, 2H), 4.19 (d, J=5.1 Hz, 2H), 3.89 (s, 3H), 3.40-3.23 (m, 2H, —OH), 1.99 (t, J=10.2 Hz, 1H), 1.59 (dd, J=14.7, 7.2 Hz, 2H), 1.42 (s, 9H), 1.32 (dd, J=14.9, 7.4 Hz, 2H), 0.91 (t, J=7.3 Hz, 3H). $^{13}$C NMR (101 MHz, $CDCl_3$) δ 166.9, 156.0, 155.5, 143.3, 138.2, 133.7, 130.2 (2C), 129.4, 128.1 (2C), 127.1, 120.3 (2C), 79.4, 52.2, 50.4, 47.7, 44.2, 30.5, 28.5 (3C), 20.2, 13.9.

5c

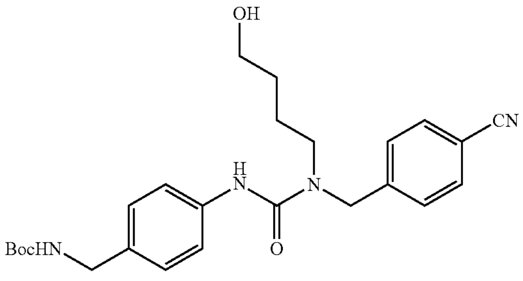

Methyl tert-Butyl (4-(3-(4-cyanobenzyl)-3-(4-hydroxybutyl)ureido)benzyl)carbamate (5c) was synthesized from 4c (120 mg, 0.58 mmol) and 2 (200 mg, 0.58 mmol) using a procedure similar to that described for the synthesis of 5a and was obtained as a colorless oil (80 mg, yield: 30%)$^1$H NMR (400 MHz, $CDCl_3$) δ 7.80 (s, 1H), 7.57 (d, J=7.9 Hz, 2H), 7.43-7.29 (m, 4H), 7.07 (d, J=7.9 Hz, 2H), 5.01 (s, 1H), 4.58 (s, 2H), 4.16 (d, J=4.5 Hz, 2H), 3.72 (s, 2H), 3.35-3.32 (m, 2H), 3.27 (br s, 1H), 1.69 (s, 2H), 1.54 (s, 2H), 1.42 (s, 9H). $^{13}$C NMR (101 MHz, $CDCl_3$) δ 156.0, 155.9, 144.1, 138.6, 133.1, 132.3 (2C), 128.0 (2C), 127.7 (2C), 120.1 (2C), 118.7, 110.9, 79.4, 62.6, 49.8, 46.8, 44.1, 28.3 (3C), 27.0, 25.5.

5d

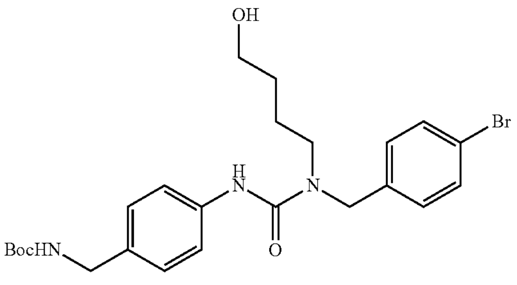

tert-Butyl (4-(3-(4-bromobenzyl)-3-(4-hydroxybutyl)ureido)benzyl)carbamate (5d) was synthesized from 4d (520 mg, 2 mmol) and 2 (680 mg, 2 mmol) using a procedure similar to that described for the synthesis of 5a and was obtained as a colorless oil (960 mg, 95%). $^1$H NMR (400 MHz, DMSO-$d_6$) δ 8.35 (s, 1H), 7.52 (d, J=8.3 Hz, 2H), 7.37 (d, J=8.1 Hz, 2H), 7.29 (br. t, 1H), 7.22 (d, J=8.3 Hz, 2H), 7.08 (d, J=8.1 Hz, 2H), 4.52 (s, 1H), 4.48 (br t, 2H), 4.03 (d, J=5.6 Hz, 2H), 3.39-3.37 (m, 2H), 3.29-3.27 (m, 2H), 1.58-1.46 (m, 2H), 1.45-1.35 (m, 2H), 1.36 (s, 9H).

(6a)

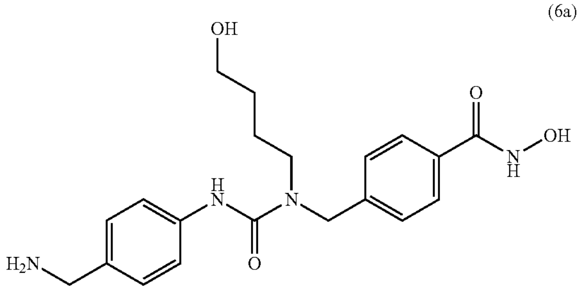

Suprastat 4-((3-(4-(Aminomethyl)phenyl)-1-(4-hydroxybutyl)ureido)methyl)-N-hydroxybenz-amide (6a, Suprastat). (i) In a round bottom flask, NaOH (68 mg, 1.69 mmol) was dissolved in 50% aqueous $NH_2OH$ (0.7 mL, approx. 50 equiv.) at 0° C. A solution of 5a (200 mg, 0.43 mmol) in 1:1 THF/MeOH (2/2 mL) was added dropwise and stirring was continued for 30 min while warming to room temperature. The solution was neutralized with 2N HCl and extracted with EtOAc (10 mL×3). The combined organic layers were washed with brine, dried over $Na_2SO_4$, and concentrated under vacuum. The crude product was used directly in next step without further purification; (ii) The crude product was dissolved in THE (2 mL) followed by an addition of TFA (3 mL) at room temperature. The resulting mixture was stirred at room temperature for 0.5 h, and then the excess solvent was removed under vacuum. The crude product was purified via preparative HPLC and lyophilized to afford 6a as a white powder (62 mg, TFA salt, purity: 95%, yield: 29% over two steps). $^1H$ NMR (500 MHz, DMSO-$d_6$) δ 11.17 (br s, 1H), 8.51 (s, 1H), 8.07 (br s, 3H, $NH_3$), 7.72 (d, J=8.7 Hz, 2H), 7.50 (d, J=8.7 Hz, 2H), 7.32 (d, J=6.6 Hz, 2H), 7.30 (d, J=7.0 Hz, 2H), 4.61 (s, 2H), 3.94 (q, J=5.8 Hz, 3H), 3.39 (t, J=6.4 Hz, 2H), 3.33 (t, J=7.4 Hz, 2H), 1.54 (ddd, J=9.2, 6.4, 2.5 Hz, 2H), 1.41 (dt, J=8.7, 6.5 Hz, 2H). $^{13}C$ NMR (126 MHz, DMSO-$d_6$) δ 164.0, 155.1, 142.2, 140.8, 131.4, 129.1 (2C), 127.01 (2C), 126.97 (2C), 126.9, 119.7 (2C), 60.6, 49.0, 46.3, 42.0, 29.4, 24.6. ESI HRMS calc. for $C_{20}H_{25}N_4O_4$: [M−H], m/z 385.1881; found: 385.1871.

6b

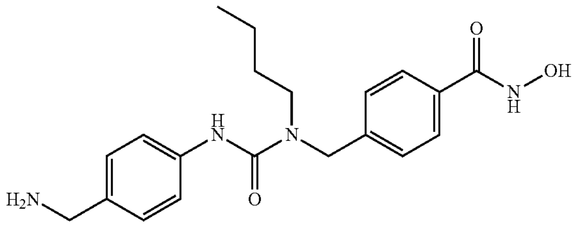

4-((3-(4-(Aminomethyl)phenyl)-1-butylureido)methyl)-N-hydroxybenzamide (6b) was synthesized from 5b (420 mg, 0.87 mmol) using a procedure similar to that described for the synthesis of 6a and was obtained as a white solid (160 mg, TFA salt, purity: >99%, yield: 77% over two steps). $^1H$ NMR (400 MHz, DMSO-$d_6$) δ 11.17 (br s, 1H), 9.00 (br s, 1H), 8.48 (s, 1H), 8.01 (br s, 3H, $NH_3$), 7.72 (d, J=8.2 Hz, 2H), 7.50 (d, J=8.6 Hz, 2H), 7.32 (d, J=6.4 Hz, 2H), 7.30 (d, J=6.8 Hz, 2H), 4.61 (s, 2H), 3.93 (t, J=5.6 Hz, 2H), 3.30-3.26 (m, 2H, overlap with water peak), 1.53-1.40 (m, 2H), 1.31-1.16 (m, 2H), 0.86 (t, J=7.3 Hz, 3H). $^{13}C$ NMR (126 MHz, DMSO-$d_6$) δ 164.0, 155.1, 142.2, 140.8, 131.4, 129.1 (2C), 127.0, 126.9 (4C), 119.8 (2C), 49.0, 46.2, 42.0, 29.9, 19.4, 13.8. ESI HRMS calc. for $C_{20}H_{25}N_4O_3$: [M−H], m/z 369.1932; found: 369.1923.

6d

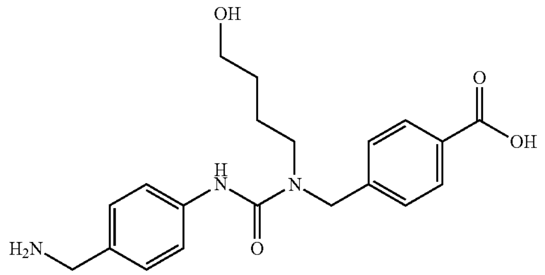

4-((3-(4-(Aminomethyl)phenyl)-1-(4-hydroxybutyl)ureido)methyl)benzoic acid (6d). To a stirred solution of 5a (62 mg, 0.13 mmol) in THF/MeOH (1/1 mL) was added 1 N NaOH solution (1 mL). Then the resulting mixture was stirred at room temperature overnight. After the completion of the reaction detected by HPLC, the reaction was acidified by 2 N HCl, and extracted with THE (15 mL×3). The combined organic extracts were washed with $H_2O$ and brine, dried over $Na_2SO_4$, and concentrated under vacuum. The crude product was dissolved in THE (2 mL) followed by an addition of TFA (3 mL) at room temperature. The resulting mixture was stirred at room temperature for additional 0.5 h, then the excess solvent was removed under vacuum. The crude product was purified via preparative HPLC and lyophilized to afford 6d as a white powder (40 mg, TFA salt, purity: 95%, yield: 63% over two steps). $^1H$ NMR (500 MHz, DMSO-$d_6$) δ 12.92 (br s, 1H), 8.53 (s, 1H), 8.07 (br s, 3H, $NH_3$), 7.91 (d, J=8.3 Hz, 2H), 7.51 (d, J=8.6 Hz, 2H), 7.37 (d, J=8.2 Hz, 2H), 7.30 (d, J=8.7 Hz, 2H), 4.65 (s, 2H), 3.94 (q, J=5.6 Hz, 2H), 3.39 (t, J=6.4 Hz, 2H), 3.34 (t, J=7.5 Hz, 2H), 1.54 (tt, J=8.2, 6.3 Hz, 2H), 1.45-1.32 (m, 2H). $^{13}C$ NMR (126 MHz, DMSO-$d_6$) δ 167.2, 155.2, 144.2, 140.8, 129.5 (2C), 129.4, 129.1 (2C), 127.1 (2C), 127.0, 119.8 (2C), 60.6, 49.1, 46.4, 42.0, 29.4, 24.6. ESI HRMS calc. for $C_{20}H_{24}N_3O_4$: $[M-H]^-$, m/z 370.1772; found: 370.1769.

6e

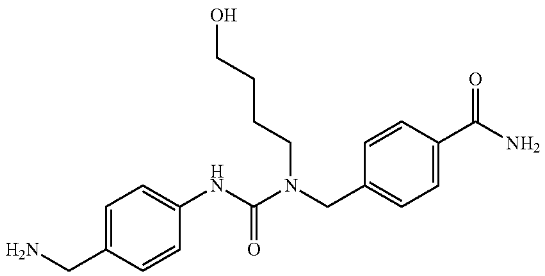

4-((3-(4-(Aminomethyl)phenyl)-1-(4-hydroxybutyl)ureido)methyl)benzamide (6e). To a stirred solution of 5c (80 mg, 0.18 mmol) in DMSO (2 mL) were added $K_2CO_3$ (2.4 mg, 0.018 mmol) and $H_2O_2$ (30%, 0.2 mL) at room temperature. The resulting mixture was stirred for 5 h. After completion of the reaction, the solution was quenched with water (5 mL) and extracted with EtOAc (10 mL×3). The organic layers were separated, washed with brine, dried over $Na_2SO_4$, and concentrated under vacuum. The crude product was dissolved in THE (2 mL) followed by an addition of TFA (3 mL) at room temperature. The resulting mixture was stirred at room temperature overnight, then the excess solvent was removed under vacuum. The crude product was purified via preparative HPLC and lyophilized to afford 6e as a white powder (30 mg, TFA salt, purity: 98%, yield: 35% over two steps). $^1$H NMR (500 MHz, DMSO-$d_6$) δ 8.51 (s, 1H), 8.06 (br s, 3H, $NH_3$), 7.92 (br s, 1H), 7.84 (d, J=8.4 Hz, 2H), 7.51 (d, J=8.6 Hz, 2H), 7.32-7.29 (m, 5H, one proton of $CONH_2$ overlaps with the signals from phenyl ring), 4.62 (s, 2H), 3.94 (q, J=5.8 Hz, 3H), 3.39 (t, J=6.4 Hz, 2H), 3.33 (t, J=7.5 Hz, 2H), 1.54 (ddd, J=12.1, 8.8, 6.4 Hz, 2H), 1.45-1.34 (m, 2H). $^{13}$C NMR (126 MHz, DMSO-$d_6$) δ 167.6, 155.1, 142.3, 140.9, 133.0, 129.1 (2C), 129.0, 127.6 (2C), 126.8 (2C), 126.7, 119.7 (2C), 60.6, 49.0, 42.0, 29.4, 24.6. ESI HRMS calc. for $C_{20}H_{27}N_4O_3$: $[M+H]^+$, m/z 371.2078; found: 371.2087.

6f

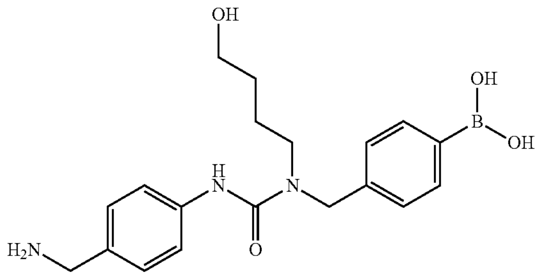

(4-((3-(4-(Aminomethyl)phenyl)-1-(4-hydroxybutyl)ureido)methyl)phenyl)boronic acid (6f). (i) To a stirred solution of 5d (510 mg, 1.0 mmol), bis(pinacolato)diboron (280 mg, 1.1 mmol), and potassium acetate (290 mg, 3 mmol) in DMF (5 mL) was added Pd(dppf)$Cl_2$ at room temperature under Argon atmosphere. After stirring at 80° C. overnight, the reaction was cooled to room temperature, and the excess solid was filtered off. The filtrate was collected, quenched with saturated $NaHCO_3$ aqueous solution (20 mL), and extracted with EtOAc (20 mL×3). The combined organic layers were washed with 10% LiCl aqueous solution, washed with brine (30 mL), dried over $Na_2SO_4$, and concentrated under vacuum. The crude was purified via flash chromatography (0-50% EtOAc/hexane) to afford the pinacol ester intermediate as a brown solid (0.25 g, yield: 44%). (ii) To a solution of the pinacol ester intermediate (240 mg, 0.44 mmol) in acetone/water (2:1, 9 mL) were added $NaIO_4$ (280 mg, 1.32 mmol) and $NH_4OAc$ (100 mg, 1.32 mmol) at room temperature. After stirring at room temperature overnight, the reaction mixture was quenched with water and extracted with EtOAc (20 mL×3). The combined organic layers were washed with brine (30 mL), dried over $Na_2SO_4$, and concentrated under vacuum. The crude product was used directly to the next step without further purification. (iii) The crude product was dissolved in THE (1 mL), followed by the addition of TFA (1 mL) at room temperature. The resulting mixture was stirred at room temperature for 0.5 h, and then the excess solvent was removed under vacuum. The crude product was purified via preparative HPLC and lyophilized to afford 6f as a white powder (190 mg, TFA salt, purity: 99%, yield: 39% over three steps). $^1$H NMR (400 MHz, DMSO-$d_6$) δ 8.49 (s, 1H), 8.06 (br s, 3H, $NH_3$), 7.74 (d, J=7.5 Hz, 2H), 7.50 (d, J=8.2 Hz, 2H), 7.30 (d, J=8.2 Hz, 2H), 7.21 (d, J=7.6 Hz, 2H), 4.57 (s, 2H), 3.95 (s, 2H), 3.48 (t, J=5.7 Hz, 2H), 3.31 (t, J=6.7 Hz, 2H), 1.61-1.57 (m, 2H), 1.46-1.43 (m, 2H). ESI IRMS calc. for $C_{19}H_{27}BN_3O_4$ $[M+H]^+$: m/z 372.2089, found: 372.2098.

Expression and Purification of HDACs 1-9 and 11

Large scale expression of human HDACs was carried out in HEK293/T17 cells essentially as described previously (see, e.g., Falkenberg et al., *Nat. Rev. Drug Discov.* 13, 673-691 (2014); or Matthias et al., *Cell Cycle* 7: 7-10 (2008)). Briefly, transiently transfected cells were harvested three days post-transfection and the cell pellets resuspended in a lysis buffer (50 mM Tris, 150 mM NaCl, 10 mM KCl, 2 mM $MgCl_2$, 10% glycerol, 0.2% NP-40, 2 Units/mL benzonase, pH 8) supplemented with a cocktail of protease inhibitors (Roche, Basel, Switzerland). Cells were lysed by sonication (30 W; 3×20 s) on ice, and the cell lysate cleared by centrifugation at 40 000×g for 30 min at 4° C. Recombinant fusion HDAC proteins were purified via Strep-Tactin affinity chromatography (IBA, Gottingen, Germany) with the elution buffer comprising 50 mM HEPES, 100 mM NaCl, 50 mM KCl, 10% glycerol, and 3 mM desthiobiotin, pH 7.5. Purified proteins were concentrated to 1 mg/mL, aliquoted, flash-frozen in liquid nitrogen, and stored at −80° C. until further use.

Determination of Inhibitory Activity Against HDACs 1-9 and 11

$IC_{50}$ values in Table 1 were determined using a fluorescence-based assay with 10 μM Ac-GAK(Ac)-AMC (HDAC 1, 2, 3, 6) or 10 μM Boc-Lys(TFA)-AMC (HDAC 4, 5, 7, 8, 9, 11) as a substrate (see, e.g., Imai et al., *Cancer Sci.* 107: 1543-1549 (2016)). Briefly, individual HDACs were preincubated with dilution series of tested inhibitors (0-100 μM) in a 384-well plate in the total volume of 40 μL for 10 min at 37° C. in a reaction buffer comprising 50 mM HEPES, 140 mM NaCl, 10 mM KCl, 1 mM TCEP, 0.1% BSA, pH 7.4. Deacetylation reaction was started by the addition of 10 μL of a 10 μM substrate into the HDAC/inhibitor mixture. Following the 30 min incubation at 37° C., the reaction was terminated by the addition of 25 μL of the trypsin solution (4 mg/mL). Fluorescence development by trypsin was carried out at 37° C. for 15 and 60 min for Ac-GAK(Ac)-AMC and Boc-Lys(TFA)-AMC substrate, respectively. Released aminomethylcoumarin was quantified using a CLARIOstar fluorimeter with the excitation and emission wavelengths set to 365 nm and 440 nm, respectively. Non-linear regression analysis was employed to calculate $IC_{50}$ values using the GraphPad Prism software. Fourteen-point $IC_{50}$ curves were generated using a 3-fold inhibitor dilution series; inhibitor concentration ranges used: 100 μM-0.063 μM for HDACs 1-5, 7-9, 11; and 3 μM-1.88 μM for HDAC6. Reactions without the enzyme or the inhibitor were used to define 0% and 100% of the HDAC activity, respectively.

Cell Culture and Antibodies

The SM1 murine melanoma cells were obtained from Dr. A. Ribas at the University of California, Los Angeles. WM164 human melanoma cells were obtained from ATCC. The cells were cultured in an incubator in RPMI 1640, 1% penicillin-streptomycin, and 10% fetal bovine serum at 37° C. with 5% $CO_2$. HDAC inhibitors including 6a-c and NextA were added at concentrations of 0.1 μM, 0.5 μM, 1 μM, 2.5 μM, 5 μM, and 10 μM, and the incubation was conducted overnight. For STAT3 phosphorylation assays, cells were pre-treated with or without HDAC6i (5 μM) for overnight followed by treatment with recombinant human IL-6 (Biolegend) for 20 min. PBS was added as a control. RAW 264.7 macrophages were purchased from ATCC and cultured in DMEM medium supplemented with 10% FBS, 1% non-essential amino acids, and 2-mercaptoethanol (50 μM). RAW macrophages were treated with 1 μM, 5 μM, and 10 μM of Suprastat overnight before collecting the lysates for immunoblot assay. Cytotoxicity assay was performed using CellTox Green (Promega, Cat #G8731) following the manufacturer's instructions, and fluorescence readings were obtained on Spectramax i3 (Molecular Devices) multimode plate reader at wavelengths EX 485 nm and EM 520 nm. SM1 cells were treated with compounds at various concentrations for 24 h to determine cytotoxicity.

Immunoblot Analysis

The cells were harvested and lysed with RIPA buffer (ThermoScientific, 89900) containing protease and phosphatase inhibitors (ThermoScientific, 78440) by sonication in Bioruptor (Diagenode) for 8 cycles of 30 seconds ON and 30 seconds OFF on high setting. To assess the expression of proteins, total protein samples were heat-denatured in SDS sample loading buffer, and 15-20 μg of protein was analysed on 4-20% SDS-PAGE gels (Bio-Rad, 456-1093). Proteins were transferred onto low fluorescence PVDF membrane (Bio-Rad, 1704274) using Trans-Blot Turbo transfer system (Bio-Rad). The membranes were blocked for 1 hour with Odyssey blocking buffer (Licor, 927-40000) followed by incubation with primary antibodies (1:1000 dilution) at 4° C. The membranes were washed in TBST buffer three times followed by incubation with near-infrared fluorophore conjugated secondary antibodies (1:10000 dilution) for 1 hour at room temperature. The membranes were scanned on Azure Biosystems C600 imager at near-infrared wavelengths. The images were analysed and processed with Image Studio™ Lite software. The antibodies used are HDAC6 (Assay biotech, C0266), α-tubulin (Cell Signaling, 3873), acetyl-α-tubulin (Cell Signaling, 3971) histone 3 (Cell Signaling, 3638S) and acetyl-histone 3 (Cell Signaling, 9649S).

Quantitative Analysis of Gene Expression

Total RNA was isolated from cells following the manufacturer's instructions of QIAzol (Qiagen, 79306). RNA quantification was done using NanoDrop One spectrophotometer (NanoDrop Technologies). Samples with absorbance at 260/280 ratios over 1.9 were used for cDNA synthesis with iScript cDNA synthesis kit (Bio-Rad, 1708891). Synthesized cDNA from 1 μg of total RNA was diluted 1:10 with nuclease-free water. The quantitative PCR analysis was performed using iQ SYBR Green Supermix (Bio-Rad, 1708882) on CFX96 real-time system (Bio-Rad). Gene expression analysis was performed using $2^{-\Delta\Delta Ct}$ method, and target mRNA levels were normalized to GAPDH expression. Cycling conditions were used as per manufacturer's instructions. Single PCR product amplification was confirmed by melting curve analysis in all the experiments performed. The sequence of primers used in the analysis are as follows:

Mice

Animal experiments involving mice were performed in accordance with protocol (#A354) approved by the Institutional Care and Use Committee (IACUC) at The George Washington University. Forty C57BL/6 female mice were purchased from the Charles River Laboratories (Wilmington, Massachusetts, USA). In vivo studies were performed using tumor cells that were passaged in vivo from mouse to mouse for a minimum of five times before tumor implantation. Mice were injected subcutaneously with $1.0\times10^6$ in vivo passaged melanoma cells suspended in 100 μL phosphate buffered saline (PBS) (Corning, 21-040-CV). Pretreatment arm was started once the tumors were palpable which was about 5 days post tumor implantation. Cages were randomly assigned to different treatment groups and mice were treated with Suprastat, anti-PD1 antibody or vehicle control. Control mice were injected intraperitoneally with 100 μL PBS as vehicle control, 15 mg/kg dose of anti-PD1 antibody (BioXcell, Clone RMP1-14), and 25 mg/kg of Suprastat. Mice were treated five days a week until tumors in the control group reached maximum size according to our IACUC protocol. Tumor volume measurements were taken alternate days using caliper measurements and calculate using the formula $L\times W^2/2$. All animal studies were performed with consideration for toxicity, and early signs of toxicity were routinely monitored. Emphasis was given to mortality, body weight, and food consumption. At the end-point postmortem evaluation, including gross visual examination of organs such as liver for hepatotoxicity, splenomegaly, and lung metastatic nodules was done for each condition.

In Vitro Evaluation of 6a-c

To evaluate the influence of each additional functional group on the potency and isoform selectivity, the potency of 6a-c along with NextA against human HDACs 1-9 and 11 was tested under optimized conditions in vitro (see, e.g., Osko et al., *J. Med. Chem.* 63: 295-308 (2020)). Results in Table 1 suggest that 6a and 6c are more potent and selective HDAC6is ($IC_{50}$=0.4 vs. 0.5 nM) with at least 290-fold selectivity over Class I isoforms HDAC1-3 and 8 and a thousand-fold selectivity over Class IIa isoforms HDAC4, 5, 7, and 9. Moreover, 6a-c did not show activity against the Class IV isoform HDAC11 up to 50 μM. It shall be noted that experimental $IC_{50}$ values in the range of 0.2-0.4 nM for HDAC6 are at the limit of our assay that uses approximately 0.6 nM concentration of the full-length enzyme (as determined by absorbance measurements at 280 nm). $IC_{50}$ values for Suprastat and 6c are thus at the limit of our assay, and these two inhibitors can theoretically have even higher potency than reported here. Overall, the inhibition data suggest that the hydroxylbutyl chain is more crucial for improving enzymatic HDAC6 potency and selectivity compared to the aminomethyl group. Additionally, the incorporation of the polar aminomethyl and hydroxylbutyl groups into the inhibitors 6a-c, increases the number of heavy atoms but decreases their clogP (calculated by SwissADME) relative to NextA (Table 3), which leads to significantly elevated lipophilic ligand efficiencies (LipE), especially 6a (LipE=7.57 (6a) vs. 6.19 (NexA)), although the ligand efficiencies (LE) of 6a and 6b are slightly lower. Taken together, compared to NextA and related analogs, Suprastat (6a) bearing both hydroxybutyl and aminomethyl moieties showed improved potency against HDAC6 and excellent selectivity over the HDAC isoforms, while it also exhibits the highest LipE value due to its significantly decreased clogP. On the other hand, the inhibitory potency of non-hydroxamate analogs 6d-f comprising carboxylic acid, amide, and boronic acid as alterative ZBGs against HDAC6 was severely compromised (Table 2), which may indicate that the additional hydrogen bonding interactions between the cap and HDAC6 pocket are not strong enough for retaining the nanomole potency without the critical hydroxamate-$Zn^{2+}$ coordination.

TABLE 1

In vitro HDAC profiles of 6a-c and NextA[a]

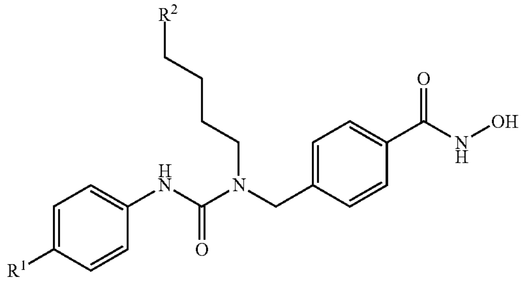

| Compound | Suprastat (6a) | | 6b | | 6c[b] | | NextA | |
|---|---|---|---|---|---|---|---|---|
| $R^1$ | $CH_2NH_2$ | | $CH_2NH_2$ | | H | | H | |
| $R^2$ | OH | | H | | OH | | H | |
| Isoform | $IC_{50}$, nM | SI[c] | $IC_{50}$, nM | SI | $IC_{50}$, nM | SI | $IC_{50}$, nM | SI |
| HDAC6 | 0.4 ± 0.0 | 1 | 0.9 ± 0.7 | 1 | 0.5 ± 0.4 | 1 | 1.6 ± 0.4 | 1 |
| HDAC1 | 117 ± 10 | 293 | 80 ± 45 | 89 | 148 ± 9 | 296 | 151 ± 20 | 94 |
| HDAC2 | 176 ± 21 | 440 | 281 ± 28 | 312 | 268 ± 16 | 536 | 276 ± 96 | 173 |
| HDAC3 | 352 ± 2 | 880 | 443 ± 108 | 492 | 581 ± 18 | 1,160 | 1,420 ± 145 | 887 |
| HDAC4 | 8,250 ± 1,350 | 20,600 | 23,100 ± 226 | 25,700 | 14,000 ± 1,380 | 27,900 | 14,800 ± 1,700 | 9,250 |
| HDAC5 | 3,420 ± 373 | 8,550 | 10,100 ± 162 | 11,200 | 9,130 ± 119 | 18,300 | 6,620 ± 2,600 | 4,140 |
| HDAC7 | 1,470 ± 56 | 3,680 | 9,000 ± 1,110 | 10,000 | 1,930 ± 70 | 3,870 | 2,430 ± 300 | 1,520 |
| HDAC8 | 498 ± 58 | 1,250 | 614 ± 58 | 682 | 478 ± 97 | 956 | 988 ± 264 | 618 |
| HDAC9 | 6,270 ± 177 | 15,700 | 17,300 ± 4,990 | 19,200 | 29,700 ± 4,190 | 59,50 | 2,000 ± 770 | 1,250 |
| HDAC11 | >50,000 | — | >50,000 | — | >50,000 | — | 10,600 ± 2,200 | 6,630 |

[a] $IC_{50}$ values are the mean of two experiments ± SEM calculated by non-linear regression analysis from experimental $v_i/v_0$ values for each HDAC isoform.

[b] 6c was originally published as compound 7b in Tavares *et al., ACS Med. Chem. Lett. 8*: 1031-1036 (2017).

[c] SI: HDAC6 selectivity index over other HDAC isoforms

TABLE 2

Inhibitory potency of NextA and its analogues 6d-f against HDAC 1 and HDAC6

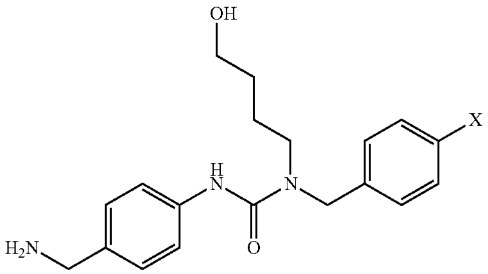

| Compound | X | HDAC6 ($IC_{50}$, nM) | HDAC1 ($IC_{50}$, nM) | HDAC1/6 |
|---|---|---|---|---|
| Suprastat (6a) | 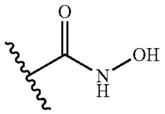 [SMILES: *C(=O)NO] | 0.4 ± 0.0 | 117 ± 10 | 293 |
| 6d | 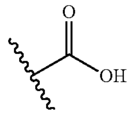 [SMILES: *C(=O)O] | 16,755 | N.D.[g] | N.D. |
| 6e | 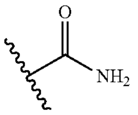 [SMILES: *C(N)=O] | >30,000 | N.D. | N.D. |

TABLE 2-continued

| | | | | |
|---|---|---|---|---|
| 6f | 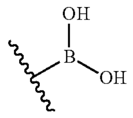 [SMILES: *B(O)O] | >30,000 | N.D. | N.D. |
| Vorinostat | — | 6.7 ± 1.0 | 31 ± 12 | 5 |

As a part of the initial ADME profiling, the stability of studied compounds was determined in PBS, simulated gastric fluid (SGF), human plasma, and liver microsomes, as well as protein binding in human plasma (Table 3). Overall, the stability of Suprastat (6a) is very good ranging from >24 hours in PBS to the half-life of 173 min in rat liver microsomes. In line with predicted physicochemical characteristics, plasma binding of Suprastat is very low (1.9% of plasma protein-bound fraction), which is beneficial for elevating free drug concentration in vivo, compared to the more hydrophobic parent compound NextA (89%), while plasma-bound fractions of singly modified derivatives 6b and 6c are approximately 50%.

TABLE 3

Ligand efficiency and in vitro ADME profiling of 6a-c and NexA

| Compound | 6a | 6b | 6c | NexA |
|---|---|---|---|---|
| clog $P_{o/w}$ [a] | 1.23 | 2.21 | 1.82 | 2.61 |
| LE[b] | 0.47 | 0.47 | 0.50 | 0.49 |
| LipE[c] | 7.57 | 6.59 | 6.98 | 6.19 |
| PBS stability ($t_{1/2}$, h) | >24 | >24 | >24 | >24 |
| SGF stability ($t_{1/2}$, h) | >5 | >5 | >5 | >5 |
| Human plasma stability ($t_{1/2}$, h) | >5 | >5 | >5 | >5 |
| Rat liver microsomes ($t_{1/2}$, min) | 177 ± 6 | 173 ± 71 | 198 ± 32 | 423 ± 104 |
| Human plasma binding (%) | 1.9 ± 3.5 | 47 ± 2.0 | 48 ± 0.9 | 89 ± 0.7 |

[a] clog $P_{o/w}$ values were calculated by SwissADME (http://www.swissadme.ch/).
[b]LE: ligand efficiency = 1.4 × pIC50/number of heavy atoms.
[c]LipE: lipophilic ligand efficiency = $pIC_{50}$ − clog $P_{o/w}$.
[d]Data are presented as mean with standard error.

In Vitro Characterization of 6a-c in Melanoma Cells

Figure 1E:
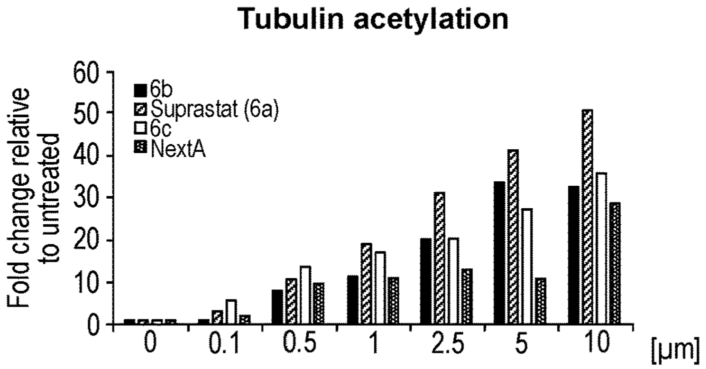
FIG. 1E is a bar graph showing the densitometric analyses of the Ac-α-tubulin band with increasing concentrations ranging from 0.1 μM to 10 μM of Suprastat (6a), compound 6b, compound 6c, and NextA.
Figure 1F:
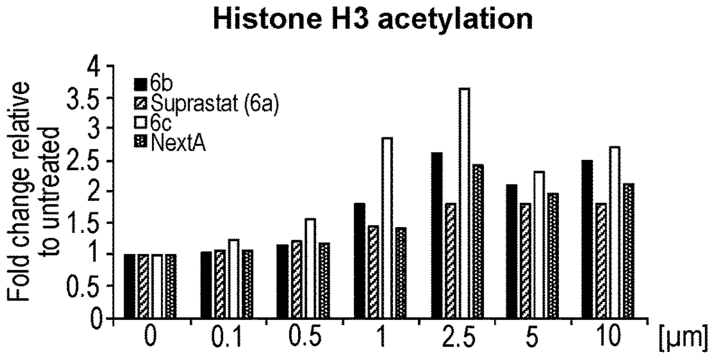
FIG. 1F is a bar graph showing the densitometric analyses of the Ac—H3 band with increasing concentrations ranging from 0.1 μM to 10 μM of Suprastat (6a), compound 6b, compound 6c, and NextA.
Figure 2:
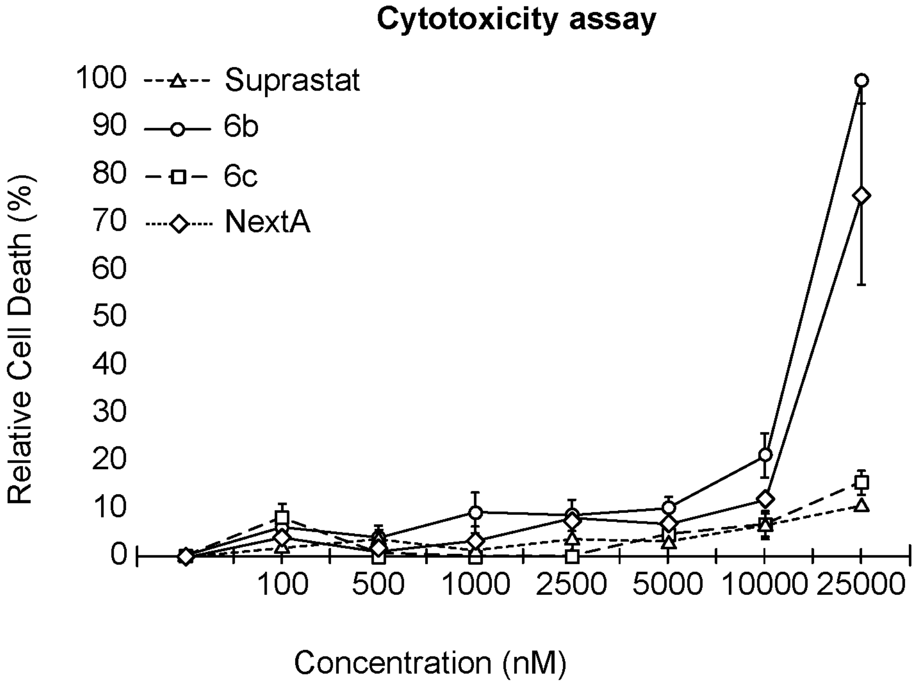
FIG. 2 is a line graph showing the cytotoxicity assay with increasing concentrations of Suprastat (6a), compound 6b, compound 6c, and NextA.

To assess the potency and isoform selectivity of 6a-c in cells, in vitro analysis using WM164 human melanoma cell line was performed. WM164 cells are mutant for BRAF V600E; a mutation that is frequently seen in melanoma patients (see, e.g., Daina et al., *Sci. Rep.* 7: 42717 (2017)). WM164 cells were treated with 6a-c and NextA with a concentration range from 0.1 to 10 μM, respectively. Their abilities to increase the levels of acetylated α-tubulin (Ac-α-tubulin) were determined by immunoblot analysis and compared side-by-side. FIGS. 1A-D show an increase in Ac-α-tubulin with increasing concentrations of HDAC6is but with varying magnitudes (FIG. 1E). However, the increase in Ac-α-tubulin was also associated with a slight increase in the levels of acetylated histone H3 (Ac—H3) albeit at higher concentrations (FIG. 1F). Treatment with Suprastat led to the highest Ac-α-tubulin level from 0.1 to 10 μM and the most significant elevation at 10 μM compared to other HDAC6is. At higher concentrations, a slight increase in the levels of Ac—H3 with Suprastat was observed, but it was much lower than other HDAC6is. This data thus demonstrates that Suprastat is a highly selective and potent HDAC6 inhibitor. Based on the concentration range for the α-tubulin/histone acetylation experiments, additional cytotoxicity assay was performed in SM1 murine melanoma cells. The results shown in FIG. 2 demonstrated that NextA and 6b started to induce cytotoxicity at the concentration of 10 μM, while Suprastat and 6c were not cytotoxic upon to 25 μM.

Functional Characterization of Suprastat

Figure 3B:
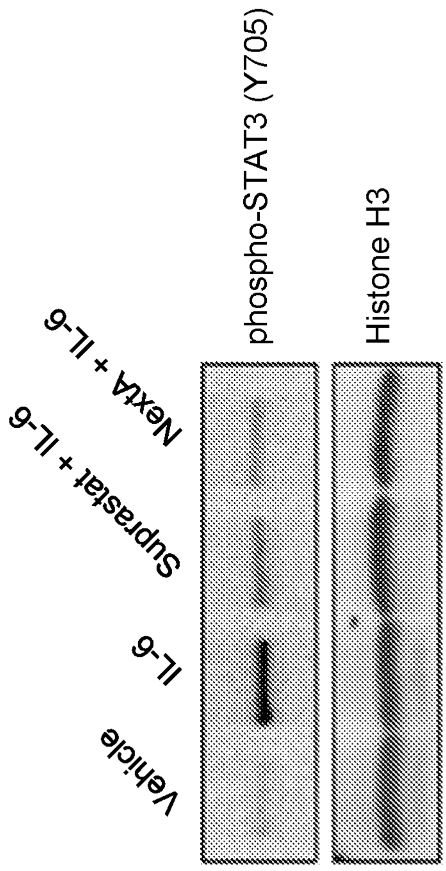
FIG. 3B is an illustration showing the immunoblot analysis of WM164 murine melanoma cells pre-treated with 5 μM of Suprastat or NextA followed by treatment with IL-6 (30 ng/mL) for 20 min.
Figure 3A:
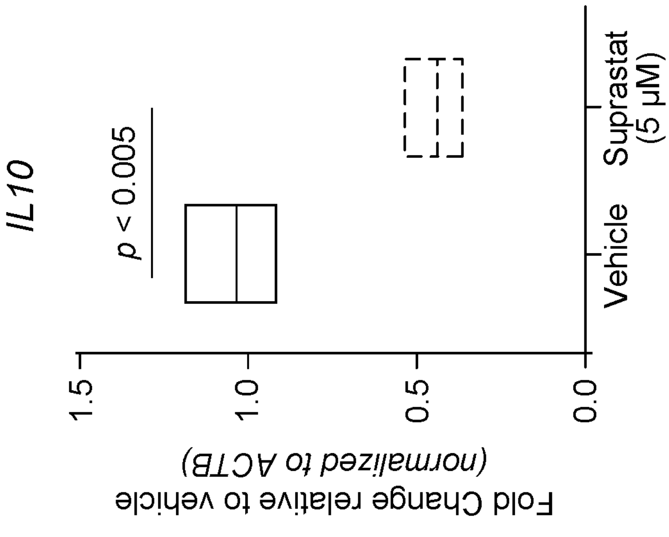
FIG. 3A is a boxplot graph showing the IL10 gene expression determined by quantitative PCR in bone marrow-derived macrophages exposed to interferon-gamma (20 ng/mL) and LPS (100 ng/mL) after treatment with Suprastat.
Figure 4A:
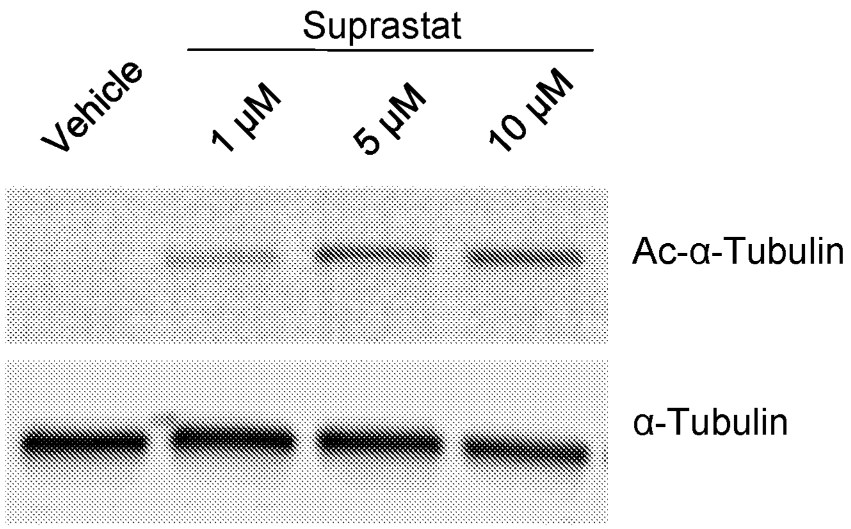
FIG. 4A is an illustration showing the immunoblot analysis of RAW 264.7 macrophages treated with increasing concentrations of Suprastat. Band intensities quantified and represented as fold change relative to vehicle indicates a dose-dependent effect of Suprastat on α-tubulin acetylation.
Figure 4B:
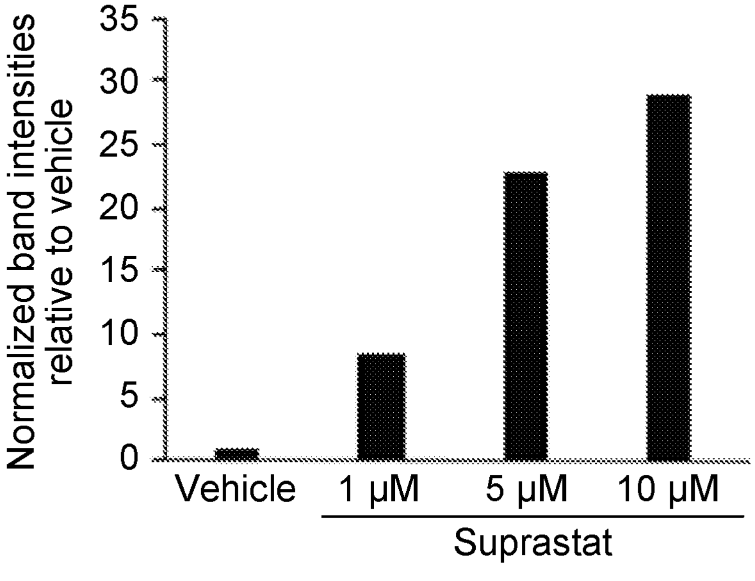
FIG. 4B is a bar graph of RAW 264.7 macrophages treated with increasing concentrations of Suprastat.

Immune cells, such as macrophages, are a major cellular component of the tumor microenvironment. Tumor-associated macrophages are often tumor promoting by secreting anti-inflammatory cytokines such as TGFβ and IL-10. It was previously established that HDAC6 forms a complex with STAT3, and either pharmacological inhibition or shRNA mediated knockdown of HDAC6 decreased STAT3 recruitment at the IL10 promoter region in antigen-presenting cells (see, e.g., Cheng et al., *J. Immunol.* 193: 2850-2862 (2014)). In line with these experiments, as shown in FIG. 3A, treatment of mouse bone marrow-derived macrophages with 5 μM Suprastat resulted in decreased expression of IL10 gene compared to vehicle-treated macrophages as determined by mRNA quantification. IL10 gene expression is normalized to β-actin (ACTB) as the reference gene. A dose-dependent increase in the levels of Ac-α-tubulin in RAW 264.7 macrophages (FIG. 4) was observed when they were treated with increasing concentrations (1, 5, and 10 μM) of Suprastat, indicating that Suprastat affects macrophages and melanoma cells in a similar fashion. Furthermore, as indicated in FIG. 3B, immunoblot analysis of lysates obtained from WM164 melanoma cells pre-treated with either Suprastat or NextA followed by exposure to IL-6 cytokine (30 ng/mL) for 20 min resulted in decreased Y705 phosphorylation of STAT3 compared to IL-6 alone. This result indicates that Suprastat, similar to NextA, mediates immunomodulatory effects by affecting HDAC6 interaction with the STAT3 transcription factor.

In Vivo Combination Study with Immunotherapy

Figure 5A:
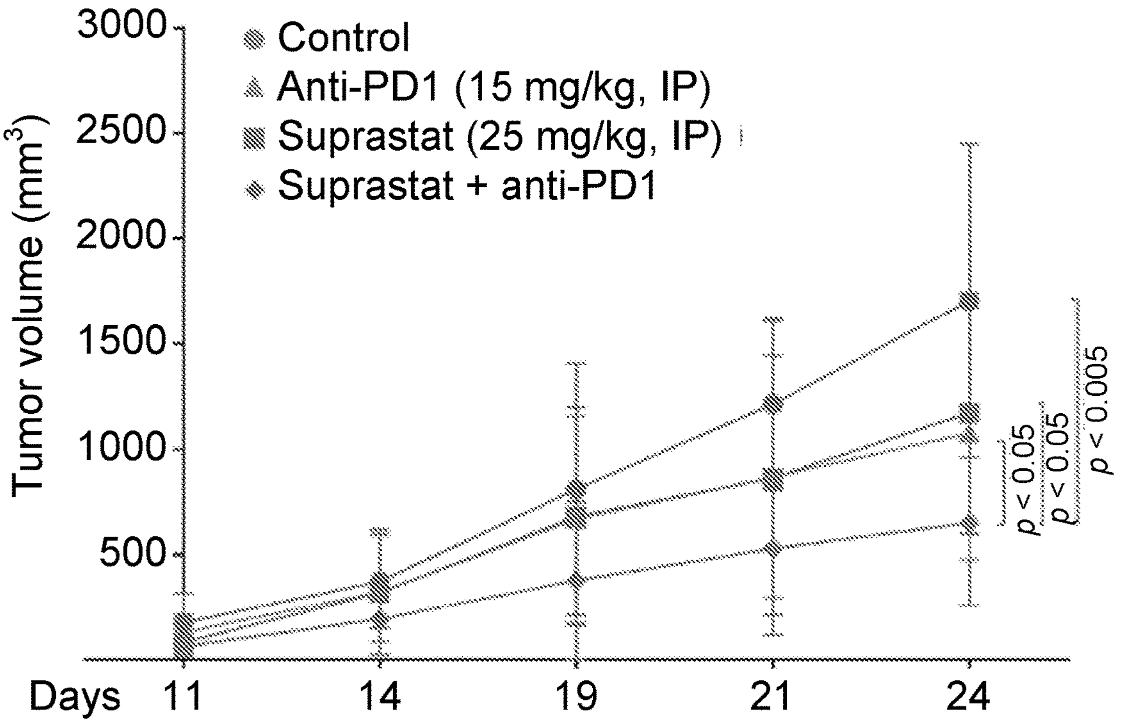
FIG. 5A is a line graph showing cumulative tumor growth rates in C57BL/6 mice (n=10) after treatment with Suprastat, anti-PD1 therapy, or a combination of both. Tumor growth rates of treatment groups were compared to control groups treated with PBS.
Figure 5B:
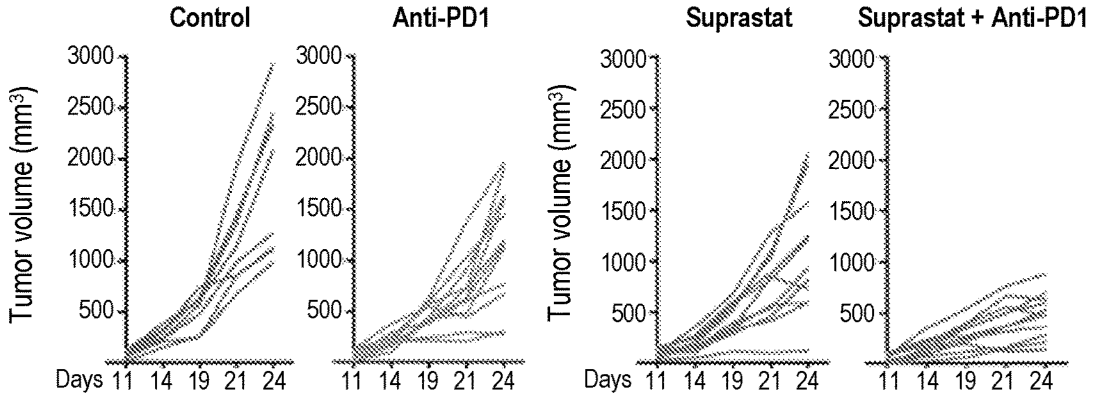
FIG. 5B are four spider graphs showing the tumor growth rates of individual mice after treatment with Suprastat,anti-PD1 therapy, or a combination of both.

Immunotherapy is emerging as a primary treatment modality for solid tumors; however, patients will often develop resistance, and currently, there is a need for combination therapies to increase the effectiveness of immunotherapy while overcoming resistance (see, e.g., O'Donnell et al., *Cancer Treat Rev.* 52: 71-81 (2017)). Using the syngeneic SM1 murine melanoma model, it was previously demonstrated that pre-treatment with NextA significantly decreased tumor size in C57BL/6 mice. These mice have an active immune system, which enables us to test immune checkpoint inhibitors such as anti-PD1 therapy. The combination of NextA and anti-PD1 therapy resulted in substantial control of tumor growth compared to single-arm therapies, suggesting that HDAC6 inhibition plays a significant role in enhancing anti-tumor immunity. Following a similar approach, C57BL/6 mice harboring SM1 melanoma tumors were administered 25 mg/kg of Suprastat intraperitoneally (IP) before starting the anti-PD1 immune checkpoint blockade therapy (15 mg/kg, IP). The pre-treatment modality was performed to pre-condition the tumor microenvironment (TME) in a manner conducive to eliciting an anti-tumor immune response. As shown in FIG. 5A, compared to the control (PBS) group, single-arm therapies with Suprastat similarly reduced the tumor burden as indicated by the tumor volume. However, a significant difference between Suprastat and the anti-PD1 therapy was not observed. On the contrary, a combination of Suprastat and anti-PD1 therapy showed a substantial decrease in tumor burden compared to control and single therapy groups, suggesting that pre-treatment with Suprastat enhances the anti-tumor immune response resulting from the anti-PD1 therapy. FIG. 5B shows the tumor growth of each mouse in the respective treatment groups. The data thus far indicate that Suprastat has immunomodulatory effects in vivo, and in combination with anti-PD1 therapy significantly enhances the anti-tumor immune response. It was noted that the Suprastat and anti-PD1 therapy combined group exhibited enhanced inhibitory effects on the tumor growth before Day 14 compared to other groups. On the contrary, the combination of NextA and anti-PD1 therapy started to exhibit distinct antitumor effects after Day 20 relative to single therapy groups in our previous studies (see, e.g., Knox et al., *Sci. Rep.* 9: 6136 (2019)), suggesting that Suprastat is capable of promoting the immunotherapy at an earlier stage.

Immunomodulatory Properties of Suprastat

Figure 6D:
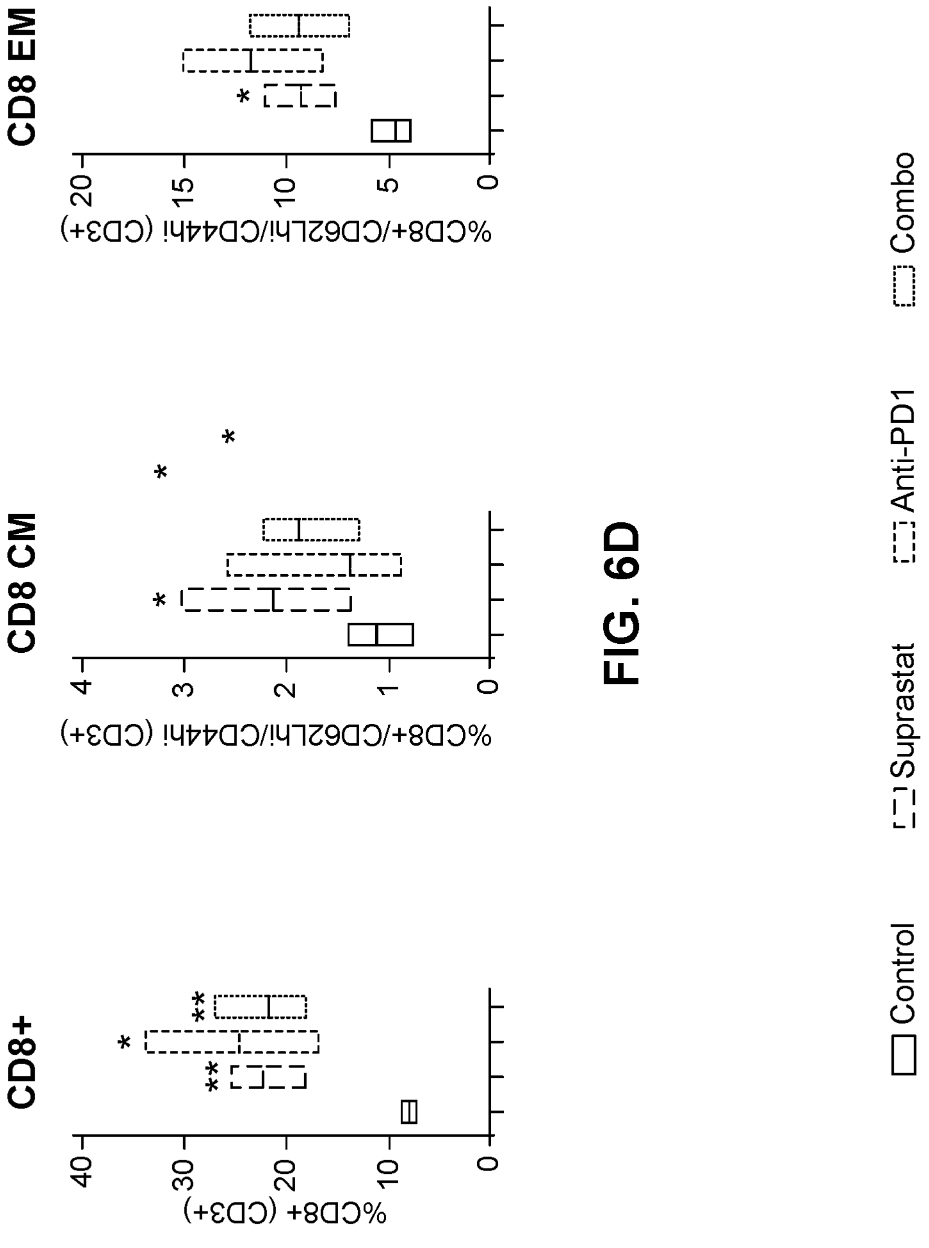
FIG. 6D is a boxplot graph showing T-cells (CD8+, CD8 CM and CD8 EM) stained with cell surface markers and analyzed by multi-color flow cytometry after treatment with Suprastat or anti-PD1 therapy or a combination of both.
Figure 6E:
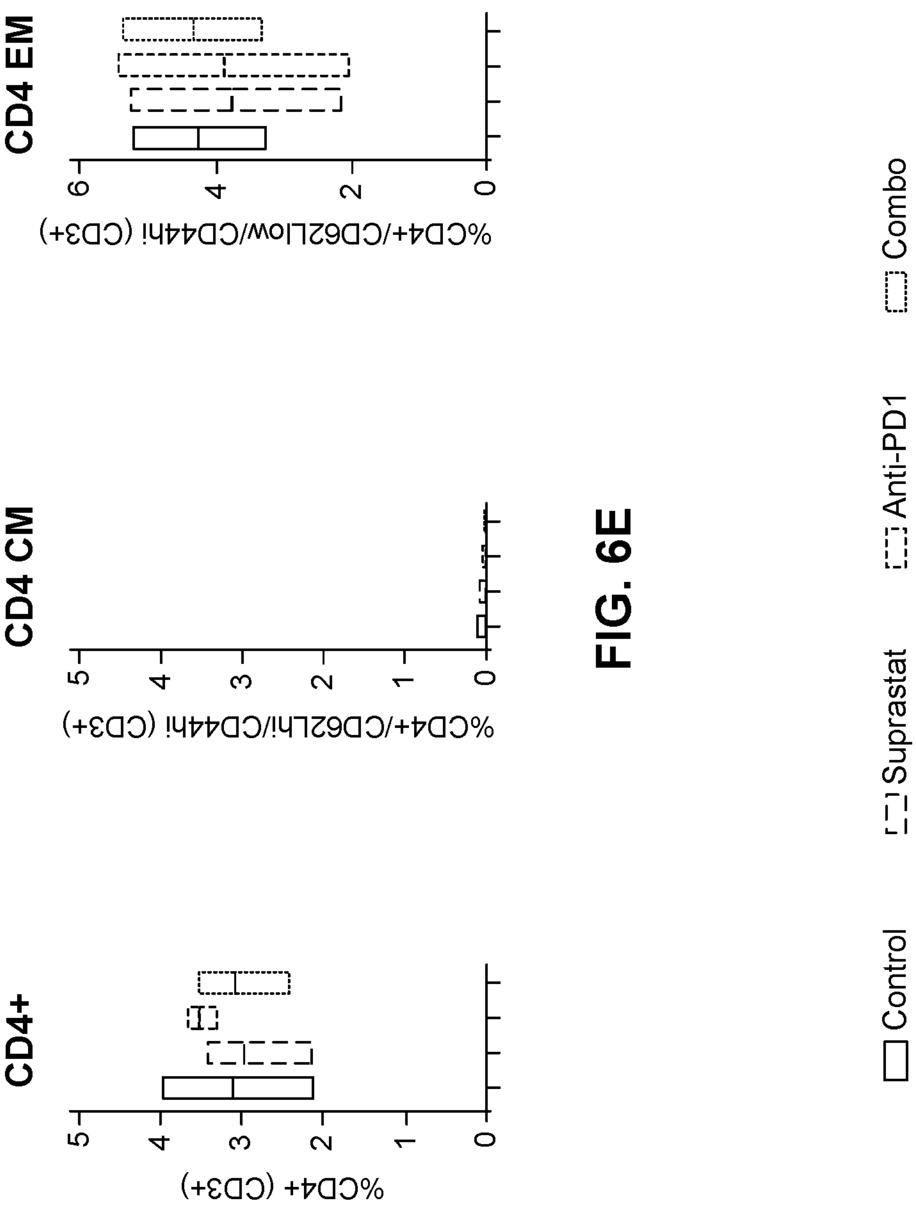
FIG. 6E is a boxplot graph showing T-cells (CD4+, CD4 CM and CD4 EM) stained with cell surface markers and analyzed by multi-color flow cytometry after treatment with Suprastat or anti-PD1 therapy or a combination of both.
Figures 6F, 6G, 6H:
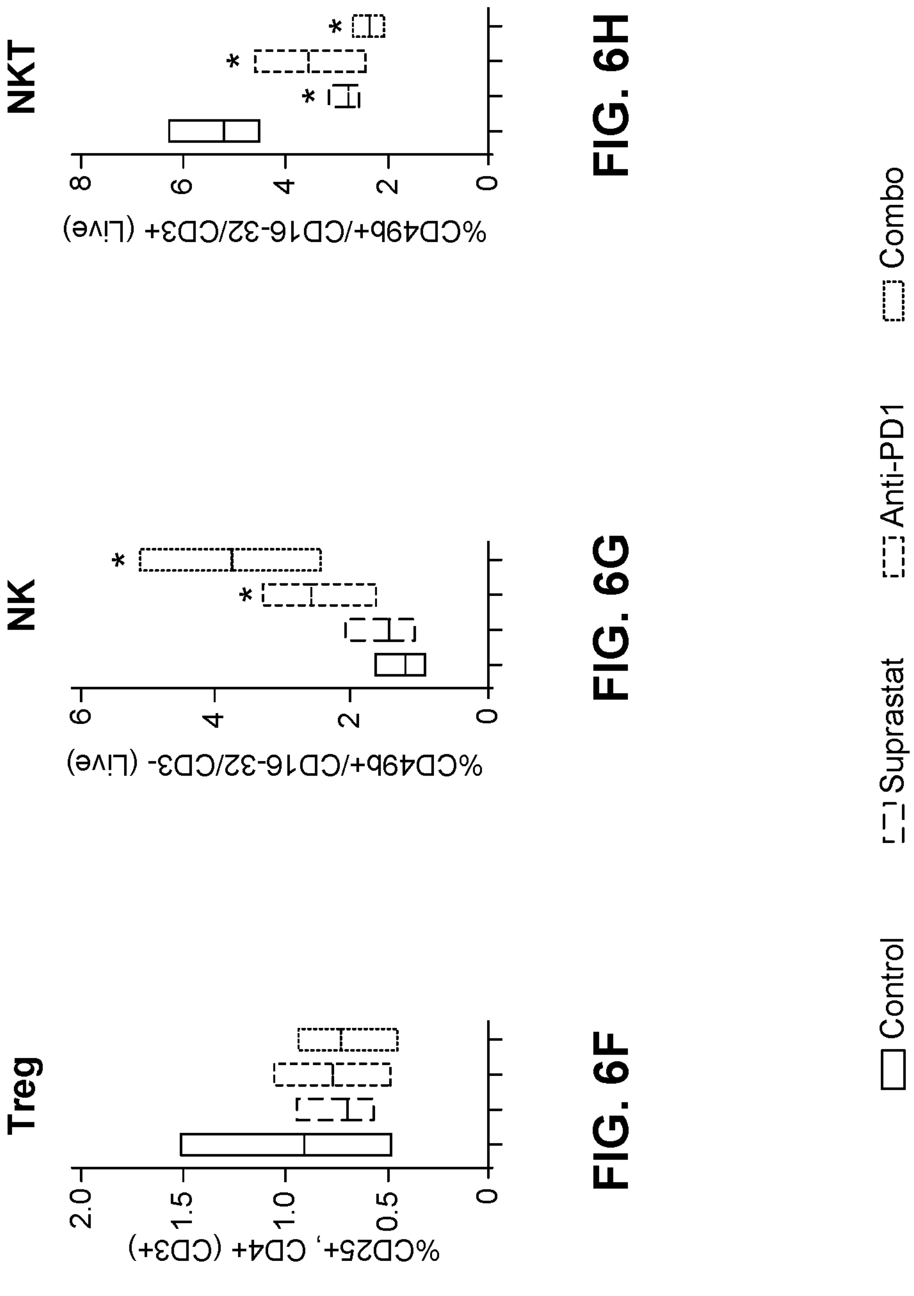
FIG. 6F is a graph showing T-cells (Treg) stained with cell surface markers and analyzed by multi-color flow cytometry after treatment with Suprastat or anti-PD1 therapy or a combination of both.
FIG. 6G is a boxplot graph showing NK cells stained with cell surface markers and analyzed by multi-color flow cytometry after treatment with Suprastat or anti-PD1 therapy or a combination of both.
FIG. 6H is a boxplot graph showing NKT cells stained with cell surface markers and analyzed by multi-color flow cytometry after treatment with Suprastat or anti-PD1 therapy or a combination of both.

To understand the immunomodulatory properties of Suprastat, a comprehensive immune cell phenotyping by flow cytometry was performed. The number of F4/80+ CD80+H2+ anti-tumor M1 macrophages as a percentage of CD45+ cells did not significantly change in all of the treatment groups (FIG. 6A). However, Suprastat significantly decreased $F_{4/80}$+CD206+ pro-tumor M2 macrophages (FIG. 6B), thus shifting the balance towards an anti-tumor immune response as indicated by the significantly higher M1/M2 ratio (FIG. 6C) in the Suprastat and combination groups relative to control and anti-PD1 groups. Interestingly, the enhanced M1/M2 ratio in the combination group was not observed in our prior work with NextA. (see, e.g., Knox et al., *Sci. Rep.* 9: 6136 (2019)). Analysis of lymphoid cells indicates a significant increase in CD8+ effector T-cells and effector memory cells in all of the treated groups compared to the control group (FIG. 6D) in which the increased folds were more significant in all the groups than prior studies performed with NextA. However, only an increase in the percentage of CD8+ central memory (CM) cells with the Suprastat treated group was observed, suggesting that it can enhance the effector memory function of CD8 T-cells for prolonged anti-tumor immune responses. Analysis of CD4+ T-cells did not show any significant changes in central memory (CM) or effector memory (EM) functions (FIG. 6E). A significant change in immunosuppressive T-regs (FIG. 6F) was not observed. Further analysis of natural killer (NK) cells demonstrated an increase in the anti-PD1 group and combination group but did have a positive trend in the Suprastat group (FIG. 6G), which was not observed in previous combination studies using NexA. (see, e.g., Knox et al., *Sci. Rep.* 9: 6136 (2019)). NK T-cells were significantly decreased in all treatment groups compared to the control group (FIG. 6H), which may be speculated to a significant increase in CD8+ effector T-cells. Overall, the immune cell phenotyping indicates that Suprastat has improved immunomodulatory properties by decreasing pro-tumoral M2 macrophages and increasing the infiltration of anti-tumor CD8+ effector T-cells and memory cells relative to parent compound NextA, responsible for the promoted immunomodulatory effects in vivo and the improved anti-tumor immune response in combination with anti-PD1 therapy.

CONCLUSIONS

In comparison with other related analogs, Suprastat shows the potent HDAC6 activity, isoform selectivity, and an ability to selectively enhance the levels of acetylated tubulin rather than obviously affecting histone acetylation. The additional polar functional groups on Suprastat decrease its lipophilicity, which leads to a higher ligand efficiency and plasma protein binding while maintaining good metabolic stability in different mediums. The in vivo combination studies with PD-1 antibody reveal that Suprastat significantly improves the therapeutic outcome through its immunomodulatory properties.

REFERENCES

1. S. Zhao, W. Xu, W. Jiang, W. Yu, Y Lin, T. Zhang, J. Yao, L. Zhou, Y Zeng, H. Li, Y Li, J. Shi, W. An, S. M. Hancock, F. He, L. Qin, J. Chin, P. Yang, X. Chen, Q. Lei, Y Xiong and K. L. Guan, *Science,* 2010, 327, 1000-1004.
2. Q. Wang, Y Zhang, C. Yang, H. Xiong, Y Lin, J. Yao, H. Li, L. Xie, W. Zhao, Y Yao, Z. B. Ning, R. Zeng, Y Xiong, K. L. Guan, S. Zhao and G. P. Zhao, *Science,* 2010, 327, 1004-1007.
3. C. Choudhary, B. T. Weinert, Y Nishida, E. Verdin and M. Mann, *Nat. Rev. Mol. Cell Biol.,* 2014, 15, 536-550.
4. Y Li and E. Seto, *Cold Spring Harb. Perspect. Med.,* 2016, 6.
5. T. Eckschlager, J. Plch, M. Stiborova and J. Hrabeta, *Int. J. Mol. Sci.,* 2017, 18, E1414.
6. K. J. Falkenberg and R. W. Johnstone, *Nat. Rev. Drug Discov.,* 2014, 13, 673-691.
7. P. Matthias, M. Yoshida and S. Khochbin, *Cell Cycle,* 2008, 7, 7-10.
8. Y Imai, Y Maru and J. Tanaka, *Cancer Sci.,* 2016, 107, 1543-1549.
9. S. Shen and A. P. Kozikowski, *Expert Opin. Ther. Pat.,* 2020, 30, 121-136.
10. C. Rebe and F. Ghiringhelli, *Cancers* (*Basel*), 2019, 11, 1280.
11. F. Cheng, M. Lienlaf, H. W. Wang, P. Perez-Villarroel, C. Lee, K. Woan, J. Rock-Klotz, E. Sahakian, D. Woods, J. Pinilla-Ibarz, J. Kalin, J. Tao, W. Hancock, A. Kozikowski, E. Seto, A. Villagra and E. M. Sotomayor, *J. Immunol.,* 2014, 193, 2850-2862.
12. M. Lienlaf, P. Perez-Villarroel, T. Knox, M. Pabon, E. Sahakian, J. Powers, K. V Woan, C. Lee, F. Cheng, S. Deng, K. S. M. Smalley, M. Montecino, A. Kozikowski, J. Pinilla-Ibarz, A. Sarnaik, E. Seto, J. Weber, E. M. Sotomayor, A. Villagra, *Mol. Oncol.,* 2016, 10, 735-750.
13. T. Knox, E. Sahakian, D. Banik, M. Hadley, E. Palmer, S. Noonepalle, J. Kim, J. Powers, M. Gracia-Hernandez, V. Oliveira, F. Cheng, J. Chen, C. Barinka, J. Pinilla-Ibarz, N. H. Lee, A. Kozikowski and A. Villagra, *Sci. Rep.,* 2019, 9, 6136.
14. K. V. Butler, J. Kalin, C. Brochier, G. Vistoli, B. Langley and A. P. Kozikowski, *J. Am. Chem. Soc.,* 2010, 132, 10842-10846.
15. J. H. Kalin and J. A. Bergman, *J. Med Chem.,* 2013, 56, 6297-6313.
16. R. De Vreese and M. D'Hooghe, *Eur. J. Med Chem.,* 2017, 135, 174-195.
17. X. X. Wang, R. Z. Wan and Z. P. Liu, *Eur. J. Med Chem.,* 2018, 143, 1406-1418.

18. M. Faria Freitas, M. Cuendet and P. Bertrand, *Expert Opin. Ther. Pat.,* 2018, 28, 365-381.

19. Y Miyake, J. J. Keusch, L. Wang, M. Saito, D. Hess, X. Wang, B. J. Melancon, P. Helquist, H. Gut and P. Matthias, *Nat. Chem. Biol.,* 2016, 12, 748-754.

20. N. J. Porter, A. Mahendran, R. Breslow and D. W. Christianson, *Proc. Natl. Acad Sci. U.S.A.,* 2017, 114, 13459-13464.

21. Y Hai and D. W. Christianson, *Nat. Chem. Biol.,* 2016, 12, 741-747.

22. N. J. Porter, J. D. Osko, D. Diedrich, T. Kurz, J. M. Hooker, F. K. Hansen and D. W. Christianson, *J. Med Chem.,* 2018, 61, 8054-8060.

23. S. Shen, M. Hadley, K. Ustinova, J. Pavlicek, T. Knox, S. Noonepalle, M. T. Tavares, C. A. Zimprich, G. Zhang, M. B. Robers, C. Barinka, A. P. Kozikowski and A. Villagra, *J. Med Chem.,* 2019, 62, 8557-8577.

24. K. Vogerl, N. Ong, J. Senger, D. Herp, K. Schmidtkunz, M. Marek, M. Muller, K. Bartel, T. B. Shaik, N. J. Porter, D. Robaa, D. W. Christianson, C. Romier, W. Sippl, M. Jung and F. Bracher, *J. Med Chem.,* 2019, 62, 1138-1166.

25. S. Shen, M. Svoboda, G. Zhang, M. A. Cavasin, L. Motlova, T. A. McKinsey, J. H. Eubanks, C. Barinka, and A. P. Kozikowski, ACS Med. Chem. Lett, DOI: 10.1021/acsmedchemlett.9b00560.

26. J. D. Osko, N. J. Porter, P. A. Narayana Reddy, Y C. Xiao, J. Rokka, M. Jung, J. M. Hooker, J. M. Salvino and D. W. Christianson, *J. Med Chem.,* 2020, 63, 295-308.

27. S. Bhatia, V. Krieger, M. Groll, J. D. Osko, N. Ressing, H. Ahlert, A. Borkhardt, T. Kurz, D. W. Christianson, J. Hauer and F. K. Hansen, *J. Med Chem.,* 2018, 61, 10299-10309.

28. J. D. Osko, D. W. Christianson, *Bioorg. Med. Chem. Lett,* 2020, 30, 127023.

29. J. A. Bergman, K. Woan, P. Perez-Villarroel, A. Villagra, E. M. Sotomayor and A. P. Kozikowski, *J. Med Chem.,* 2012, 55, 9891-9899.

30. K. V. Woan, M. Lienlaf, P. Perez-Villaroel, C. Lee, F. Cheng, T. Knox, D. M. Woods, K. Barrios, J. Powers, E. Sahakian, H. W. Wang, J. Canales, D. Marante, K. S. M. Smalley, J. Bergman, E. Seto, A. Kozikowski, J. Pinilla-Ibarz, A. Sarnaik, E. Celis, J. Weber, E. M. Sotomayor and A. Villagra, *Mol. Oncol.,* 2015, 9, 1447-1457.

31. Y Sixto-Lopez, M. Bello and J. Correa-Basurto, *J. Biomol. Struct. Dyn.,* 2019, 37, 4701-4720.

32. M. T. Tavares, S. Shen, T. Knox, M. Hadley, Z. Kutil, C. Barinka, A. Villagra and A. P. Kozikowski, *ACS Med Chem. Lett.,* 2017, 8, 1031-1036.

33. A. Daina, O. Michielin and V. Zoete, *Sci. Rep.,* 2017, 7, 42717.

34. A. L. Hopkins, C. R. Groom and A. Alex, *Drug Discov. Today,* 2004, 9, 430-431.

35. T. W. Johnson, R. A. Gallego and M. P. Edwards, *J. Med. Chem.,* 2018, 61, 6401-6420.

36. R. C. Koya, S. Mok, N. Otte, K. J. Blacketor, B. Comin-Anduix, P. C. Tumeh, A. Minasyan, N. A. Graham, T. G. Graeber, T. Chodon and A. Ribas, *Cancer Res.,* 2012, 72, 3928-3937.

37. J. S. O'Donnell, G. V. Long, R. A. Scolyer, M. W. Teng and M. J. Smyth, *Cancer Treat Rev.,* 2017, 52, 71-81.

What is claimed is:

1. A compound of formula Id:

Id

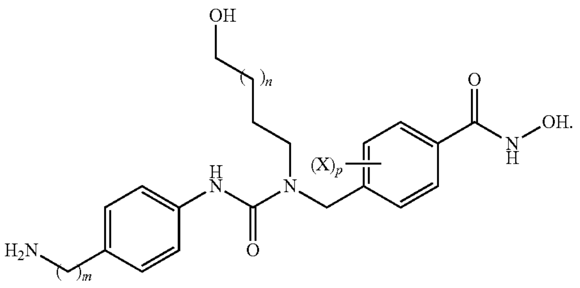

or a pharmaceutically acceptable salt thereof, wherein each X is independently hydrogen or halogen;

pis 0, 1, 2, or 3;

m is 1, 2, 3 or 4; and n is 0, 1 or 2.

2. A compound selected from the group consisting of:

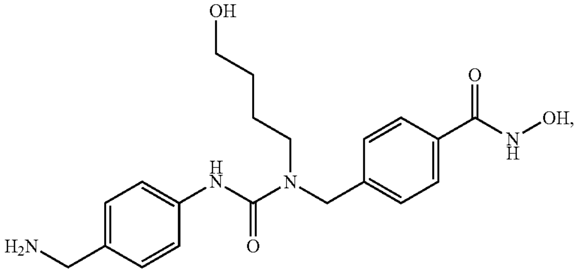

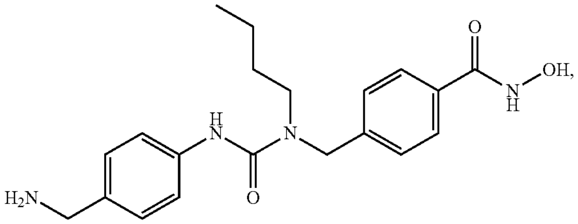

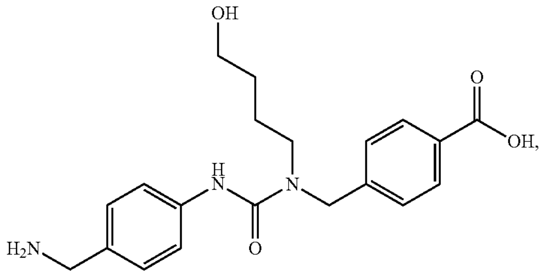

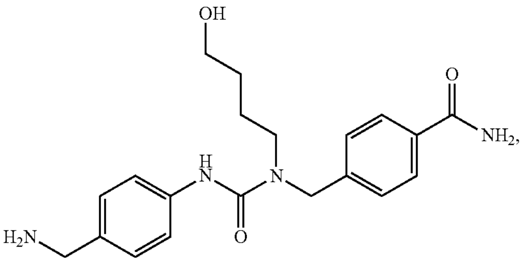

and

-continued

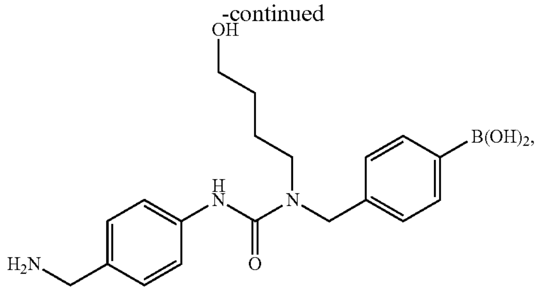

or a pharmaceutically acceptable salt thereof.

3. A composition comprising (a) the compound of claim 1, and (b) an excipient and/or pharmaceutically acceptable carrier or vehicle.

4. The composition of claim 3, further comprising a second therapeutic agent.

5. A method of treating a disease or condition in which inhibition of a histone deacetylase (HDAC) provides a benefit, the method comprising: administering to an individual in need thereof a therapeutically effective amount of the compound of claim 1.

6. The method of claim 5, wherein the HDAC is HDAC6.

7. The method of claim 5, further comprising administering to the individual a therapeutically effective amount of a second therapeutic agent useful in the treatment of the disease or condition.

8. The method of claim 7, wherein the disease or a condition is a cancer and the second therapeutic agent is one or more of a chemotherapeutic agent, radiation, and/or an immunotherapy.

9. The method of claim 8, wherein the immunotherapy comprises anti-PD1 immunotherapy.

10. The method of claim 9, wherein the anti-PD1 immunotherapy comprises administration of a PD-1 antibody, and wherein the PD-1 antibody is nivolumab, pembrolizumab, STI-A1014, or pidilzumab.

11. A method of increasing sensitivity of a cancer cell to cytotoxic effects of a radiotherapy and/or a chemotherapy, the method comprising: contacting the cancer cell with the compound of claim 1 in an amount sufficient to increase the sensitivity of the cancer cell to the radiotherapy and/or the chemotherapy.

12. A composition comprising (a) a compound of claim 2, and (b) an excipient and/or pharmaceutically acceptable carrier or vehicle.

13. The composition of claim 12, further comprising a second therapeutic agent.

14. A method of treating a disease or condition in which inhibition of a histone deacetylase (HDAC) provides a benefit, the method comprising: administering to an individual in need thereof a therapeutically effective amount of a compound of claim 2.

15. The method of claim 14, wherein the HDAC is HDAC6.

16. The method of claim 14, further comprising administering to the individual a therapeutically effective amount of a second therapeutic agent useful in the treatment of the disease or condition.

17. The method of claim 14, wherein the disease or condition is a cancer and the second therapeutic agent is one or more of a chemotherapeutic agent, radiation, and/or an immunotherapy.

18. The method of claim 17, wherein the immunotherapy comprises anti-PD1 immunotherapy.

19. The method of claim 18, wherein the anti-PD1 immunotherapy comprises administration of PD-1 antibody, and wherein the PD-1 antibody is nivolumab, pembrolizumab, STI-A1014, or pidilzumab.

20. A method of increasing sensitivity of a cancer cell to cytotoxic effects of a radiotherapy and/or a chemotherapy, the method comprising: contacting the cancer cell with a compound of claim 2 in an amount sufficient to increase the sensitivity of the cancer cell to the radiotherapy and/or the chemotherapy.

* * * * *